(12) United States Patent
Chang et al.

(10) Patent No.: US 8,476,280 B2
(45) Date of Patent: Jul. 2, 2013

(54) COMPOSITIONS AND METHODS FOR COMBATING LOWER URINARY TRACT DYSFUNCTIONS WITH DELTA OPIOID RECEPTOR AGONISTS

(75) Inventors: Kwen-Jen Chang, Chapel Hill, NC (US); Peter J. Gengo, Raleigh, NC (US); Kestutis P. Biciunas, Durnam, NC (US); Xin Ma, Carrboro, NC (US); William Pendergast, Durham, NC (US); Shyi-Tai Jan, Cary, NC (US)

(73) Assignee: Versi Group, LLC, Gladstone, NJ (US)

( * ) Notice: Subject to any disclaimer, the term of this patent is extended or adjusted under 35 U.S.C. 154(b) by 1319 days.

(21) Appl. No.: 10/434,004

(22) Filed: May 8, 2003

(65) Prior Publication Data

US 2004/0002503 A1 Jan. 1, 2004

Related U.S. Application Data

(60) Provisional application No. 60/379,186, filed on May 9, 2002.

(51) Int. Cl.
*A61K 31/4965* (2006.01)
*A61K 31/497* (2006.01)

(52) U.S. Cl.
USPC ............ 514/255.04; 514/252.12; 514/253.01; 514/730

(58) Field of Classification Search
USPC ................... 514/252.12, 730, 253.01, 255.04
See application file for complete search history.

(56) References Cited

U.S. PATENT DOCUMENTS

| | | |
|---|---|---|
| 5,552,404 A | 9/1996 | Chang et al. |
| 5,574,159 A | 11/1996 | Chang et al. |
| 5,658,908 A | 8/1997 | Chang et al. |
| 5,681,830 A | 10/1997 | Chang et al. |
| 5,807,858 A | 9/1998 | Chang et al. |
| 5,854,249 A | 12/1998 | Chang et al. |
| 5,985,880 A | 11/1999 | Chang et al. |
| 6,046,200 A | 4/2000 | Tortella et al. |
| 6,130,222 A | 10/2000 | Roberts et al. |
| 6,187,792 B1 | 2/2001 | Delorme et al. |
| 6,200,978 B1 | 3/2001 | Maw et al. |
| 6,310,103 B1 * | 10/2001 | Aberg ........................ 514/741 |
| 7,030,124 B2 | 4/2006 | Chang et al. |
| 2002/0052007 A1 | 5/2002 | Chang et al. |
| 2003/0186872 A1 | 10/2003 | Chang et al. |

FOREIGN PATENT DOCUMENTS

WO    WO02/43713 A2    6/2002

OTHER PUBLICATIONS

Andersson, Karl-Erik, "Treatment of Overactive Bladder: Other Drug Mechanisms," Urology 55 (Supplement 5A), 51-57, May 2000.
Kiss, et al., "Impaired Response to Chemical Irritation of the Urinary Tract in Mice with Disruption of the Preprotachykinin Gene," Neuroscience Letters 313 (2001) 57-60.

* cited by examiner

*Primary Examiner* — Renee Claytor
*Assistant Examiner* — Shobha Kantamneni
(74) *Attorney, Agent, or Firm* — Marianne Fuierer; Moore & Van Allen, PLLC

(57) ABSTRACT

Compositions and methods for treatment of a urinary tract dysfunction by administering to a subject in need of such treatment a pharmaceutical composition including a delta opioid receptor agonist in an amount effective to reduce the effects of the urinary tract dysfunction. The compositions may further include an additional active agent that is used to treat urinary tract dysfunctions, e.g., alpha-adrenergic agonists, anticholinergics, alpha-adrenergic antagonists and tricyclic antidepressants.

8 Claims, 8 Drawing Sheets

FIGURE 1A

TABLE 1

| Comp. No. | Structure | RBM* Ki (nM) | | GPCM* Ki (nM) |
|---|---|---|---|---|
| | | μ | δ | κ |
| 1 | Et₂N-C(O)-C₆H₄-CH(Ph)-N(piperazine with 2,5-diMe, N'-CH₂-3-F-C₆H₄) | 1524 | 2.03 | 2289 |
| 2 | Et₂N-C(O)-C₆H₄-CH(Ph)-N(piperazine with 2,5-diMe, N'-CH₂-4-F-C₆H₄) | 1024 | 4.71 | 100 |
| 3 | Et₂N-C(O)-C₆H₄-CH(3-OCH₂COOH-C₆H₄)-N(piperazine with 2,5-diMe, N'-allyl) | 83.6 | 10.3 | 451 |
| 4 | 3-F-C₆H₄-N(CH₃)-C(O)-C₆H₄-CH(Ph)-N(piperazine with 2,5-diMe, N'-allyl) | 5.75 | 13.7 | 11.6 |

| # | Structure | | | |
|---|---|---|---|---|
| 5 | 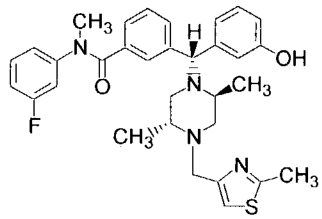 | 1.17 | 1.59 | 100 |
| 6 | 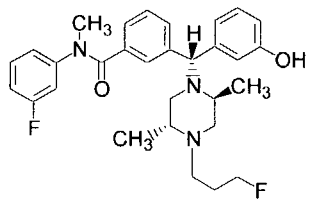 | 0.765 | 0.8 | 51 |
| 7 | 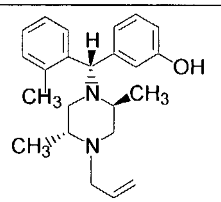 | 0.43 | 0.249 | 3.02 |
| 8 | 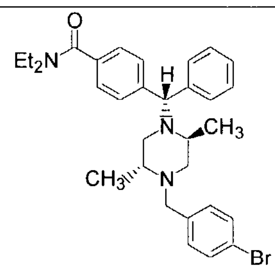 | 511 | 1.49 | 2270 |
| 9 | 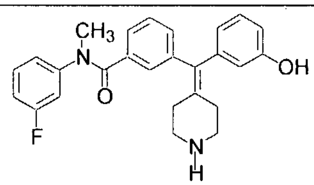 | 2.20 | 1.71 | 2.36 |
| 10 | 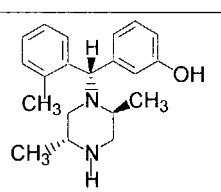 | 7.44 | 5.21 | 14.2 |

Figure 1B

| 11 | [structure: Me₂N-SO₂-phenyl-CH-(3-hydroxyphenyl)-piperazine(2-CH₃, 5-CH₃)-N-CH₂-phenyl-COOH] | 2822 | 11.0 | 3989 |
|---|---|---|---|---|
| 12 | [structure: Et₂N-CO-phenyl-CH-(3-hydroxyphenyl)-piperazine(2-CH₃, 5-CH₃)-N-CH₂-pyridyl] | 3.82 | 39.1 | 100 |

\* RBM = Rat Brain Membranes; GPCM = Guinea Pig Cerebellum Membranes

TABLE 2

| Comp. No. | Structure | Urinary Incontinence % Pre-Drug Activity | | |
|---|---|---|---|---|
| | | Dose IV (mg/kg) | Int. * | Press.* |
| 1 | Et₂N-C(=O)-C₆H₄-CH(Ph)-[piperazine with 2,5-diMe, N-(3-fluorobenzyl)] | 3.0 | 132.1 | 88.2 |
| 2 | Et₂N-C(=O)-C₆H₄-CH(Ph)-[piperazine with 2,5-diMe, N-(4-fluorobenzyl)] | 3.0 | 121.1 | 85.5 |
| 3 | Et₂N-C(=O)-C₆H₄-CH(3-OCH₂COOH-C₆H₄)-[piperazine with 2,5-diMe, N-allyl] | 3.0 | 110 | 95.3 |
| 4 | (3-F-C₆H₄)N(CH₃)-C(=O)-C₆H₄-CH(Ph)-[piperazine with 2,5-diMe, N-allyl] | 3.0 | 117 | 99.2 |

| 5 |  | 3.0 | 131.7 | 107.2 |
| 6 |  | 3.0 | 122.7 | 104 |
| 7 |  | 3.0 | 115.5 | 110.2 |
| 8 |  | 3.0 | 134.3 | 101.6 |
| 9 |  | 3.0 | 130.1 | 112.4 |
| 10 |  | 3.0 | 126 | 97 |

| 11 | [structure: Me₂N-SO₂-phenyl-CH(H)-phenyl-OH with piperazine bearing two CH₃ groups and N-CH₂-phenyl-COOH] | 3.0 | 85.2 | 99.4 |
|---|---|---|---|---|
| 12 | [structure: Et₂N-CO-phenyl-CH(H)-phenyl-OH with piperazine bearing two CH₃ groups and N-CH₂-pyridyl] | 3.0 | 111.4 | 96.0 |

\* Int. = time between bladder contractions; Press. = micturition pressure.

Figure 2C

TABLE 3

| Comp. No. | Structure | Urinary Incontinence % Pre-Drug Activity | | |
|---|---|---|---|---|
| | | Oral Dose (mg/kg) | Interval * | Pressure* |
| 1 | 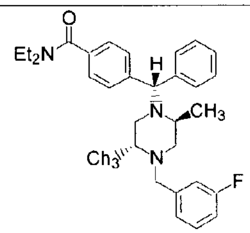 | 5 | 125 | 97 |
| | | 10 | 129 | 81 |
| | | 20 | 139 | 75 |
| 2 | 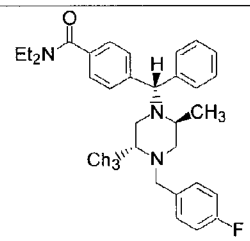 | 6 | 102 | 93 |
| | | 10 | 101 | 100 |
| | | 20 | 78 | 91 |
| 8 | 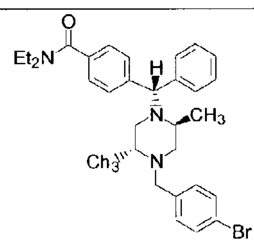 | 3 | 84 | 87 |
| | | 6 | 116 | 105 |
| | | | | |
| 11 | 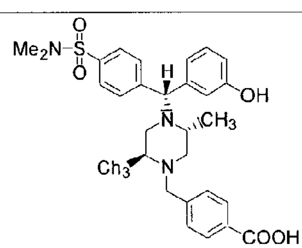 | 1 | 113 | 116 |
| | | 6 | 127 | 98 |
| | | 10 | 142 | 97 |

* Interval = time between bladder contractions; Pressure = micturition pressure.

COMPOSITIONS AND METHODS FOR COMBATING LOWER URINARY TRACT DYSFUNCTIONS WITH DELTA OPIOID RECEPTOR AGONISTS

CROSS-REFERENCE TO RELATED APPLICATIONS

This application claims priority from U.S. Provisional Patent Application No. 60/379,186 filed on May 9, 2002.

BACKGROUND OF THE INVENTION

1. Field of the Invention

The present invention relates to lower urinary tract dysfunctions in mammals, and particularly, to compositions and methods of treating urinary tract disorders using delta opioid receptor agonists to modulate contraction and relaxation of muscles controlling micturition.

2. Description of the Related Art

The National Kidney and Urologic Diseases Advisory Board estimates that urinary incontinence (UI) affects approximately 17 million people in the United States. Incontinence is a word that many people associate with the aging process. However, incontinence is not a natural part of the aging process. It can happen at any age and may be due to a number of causes, including, infection, effects of medication, muscle weakness, hormone imbalance, neurological disorders and immobility. Incontinence remains largely a neglected problem because affected people may feel embarrassed, isolated, stigmatized and unwilling to discuss the problem.

Continence requires input from the central nervous system (CNS) and integrity of lower urinary tract function. The role of the CNS is complex and not fully understood, however, it is believed that the parasympathetic, sympathetic and somatic nerves innervate the main structures involved in the maintenance of continence. The physiology of micturition (urination) is complex; however a basic understanding is necessary to appreciate the etiology and treatment of incontinence. As urine fills the bladder via the ureter, the detrusor muscle stretches allowing the bladder to expand. As the bladder fills, stretch receptors within the bladder wall are stimulated, giving the brain information regarding the amount of urine within the bladder. With low bladder volumes, the sympathetic nervous system is stimulated and parasympathetic system is inhibited resulting in internal sphincter contraction and detrusor relaxation. When the bladder is full and micturition is desired, the inhibitory signals from the brain are replaced by impulses that stimulate the parasympathetic system resulting in detrusor contraction, and inhibit the sympathetic system resulting in internal sphincter relaxation. The intravesicle pressure then rises to a point at which it exceeds the resistance within the urethra, and urine flows out of the bladder. Once the bladder is emptied, the brain again sends impulses resulting in parasympathetic inhibition and sympathetic stimulation resulting in detrusor relaxation and internal sphincter contraction. The urinary bladder is again ready to be filled with urine. Thus, because the lower urinary tract function involves so many CNS systems, the impact of medication and diseases is often difficult to predict.

Different types of urinary tract dysfunctions exhibit different symptoms. For example, dysuria includes urinary frequency, nocturia and urgency, and may be caused by cystitis, prostatitis, benign prostatic hypertrophy (BPH) or neurological disorders. Enuresis refers to the involuntary passage of urine at night or during sleep.

After the type and cause of the urinary tract dysfunction has been determined, treatment can follow, which may variously include behavioral, surgical and/or pharmacological therapeutic approaches. Behavioral therapy may include muscle exercise, adjustment of the timing or amount of fluid ingested, and/or prompted voiding. However, such methods are dependent on motivation and in some settings, such as institutions, the dedication of the nursing staff in charge of the management of incontinent patients.

Surgery may be required to correct certain disorders, such as blockage, enlarged prostate, and weak pelvic muscles but surgery is considered a last resort because of the inherent complications that may occur concurrently with surgery.

Drug therapy is more widely used as a urinary tract dysfunction-combating approach in place of behavioral therapy and surgery. A variety of therapeutic drugs have been used, including: alpha-adrenergic agonists, such as phenylpropanolamine and pseudoephedrin; anticholinergics, such as oxybutynin, propantheline, dicyclomine and tolterodine; alpha-adrenergic antagonists, such as prazosin, terazosin and doxazosin; and tricyclic antidepressants. However, these drugs may not be effective for all patients. More importantly, negative side effects of these drugs, such as dry mouth, nausea, insomnia, weakness and/or fatigue, can halt treatment or impair patient compliance. Moreover, disease states or adverse interactions with other drugs may contraindicate the use of these compounds or require lower dosages that may not be effective to combat the urinary tract dysfunction.

Thus, present day drug therapy does not successfully solve the problems associated with urinary tract dysfunction. Accordingly, the art continues to search for improved pharmaceutical agents for treatment of urinary tract dysfunctions that can be used conveniently and without embarrassment, and that do not involve the problems associated with prior therapeutic methods.

SUMMARY OF THE INVENTION

The present invention relates in one aspect to a method of combating urinary tract dysfunctions by administering to a subject in need of such treatment a pharmaceutical composition comprising a delta opioid receptor agonist in an amount effective to reduce the effects of the urinary tract dysfunction. The pharmaceutical composition may further comprise an additional active agent that has been found to be effective to treat urinary tract dysfunctions, albeit with some negative side effect(s), e.g., alpha-adrenergic agonists, anticholinergics, alpha-adrenergic antagonists and tricyclic antidepressants, whereby reduced dosages of such additional active agent enable, in combination with the delta opioid receptor agonist, ameliorate or even eliminate such negative side effect(s), or achieve other synergistic benefit by the combination.

Another aspect of the present invention relates to a method for reducing the effects of urinary tract dysfunctions comprising: administering to the subject a pharmaceutical composition comprising an effective amount of a delta opioid receptor agonist selected from the group consisting of:

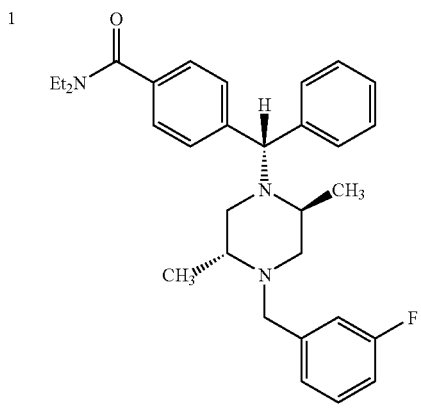
1
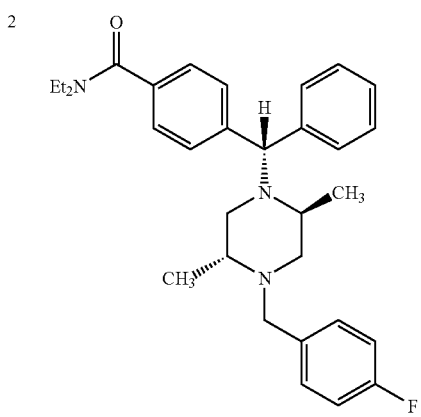
2
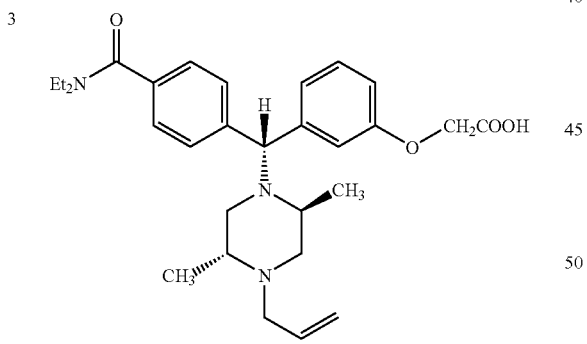
3
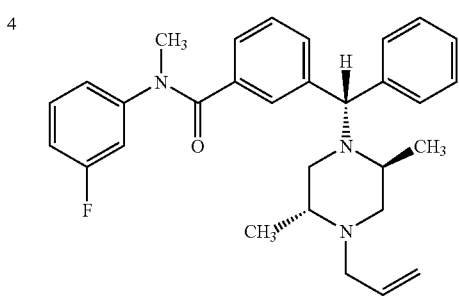
4
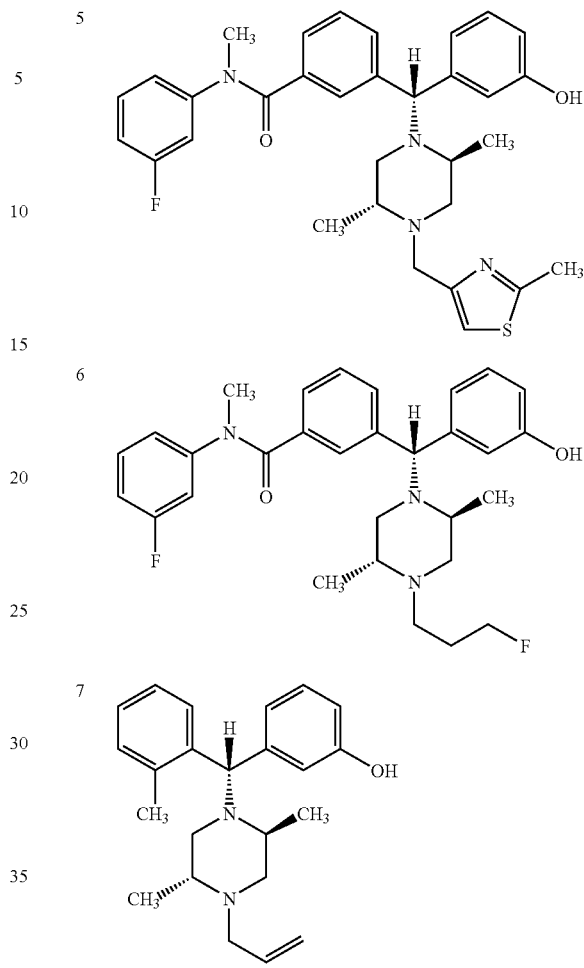
5
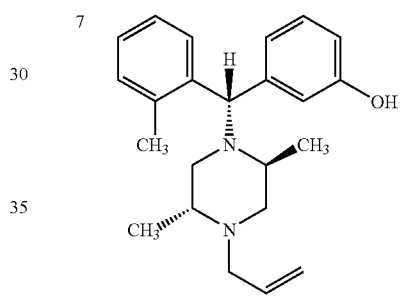
6
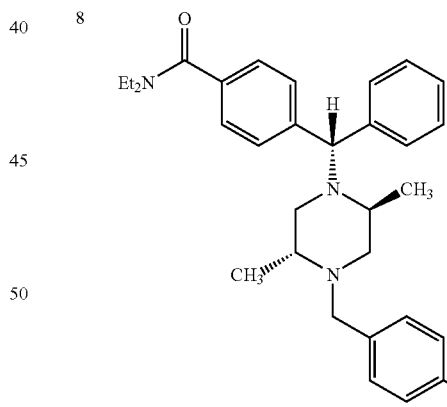
7
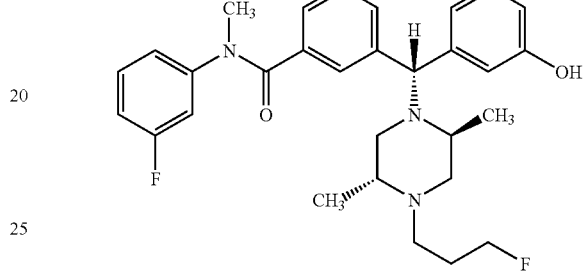
8
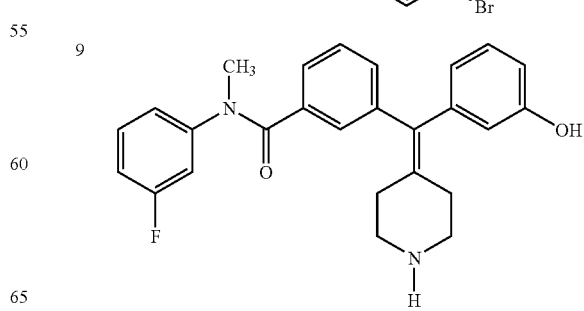
9

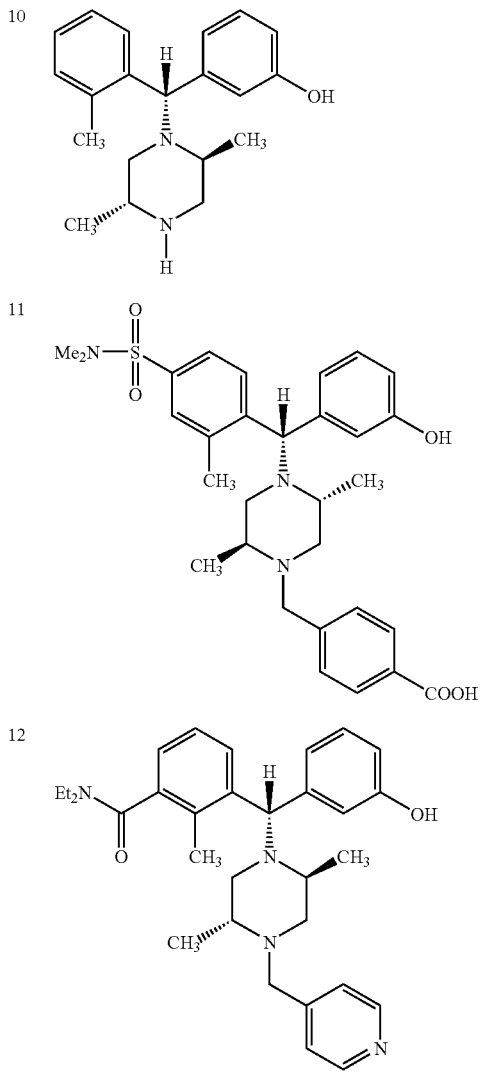

and pharmaceutically acceptable salts and esters thereof.

Another aspect of the present invention relates to a method for reducing the effects of urinary tract dysfunctions comprising: administering to the subject an effective amount of at least one compound of the formula:

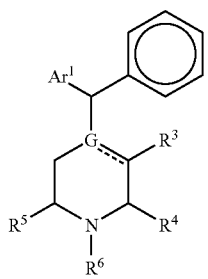

wherein:
Ar¹ is a 5- or 6-member carbocyclic or heterocyclic aromatic ring with atoms selected from the group consisting of carbon, nitrogen, oxygen and sulfur and may include thiophenyl, thiazolyl, furanyl, pyrrolyl, phenyl, or pyridyl, and having on a first carbon atom thereof a substituent Y and on a second ring carbon thereof a substituent $R^1$, Y is selected from the group consisting of:
  hydrogen;
  halogen;
  $C_1$-$C_6$ alkyl, $C_2$-$C_6$ alkenyl, $C_2$-$C_6$ alkynyl;
  $C_1$-$C_6$ haloalkyl;
  $C_1$-$C_6$ alkoxy;
  $C_3$-$C_6$ cycloalkoxy;
  sulfides of the formula $SR^8$ where $R^8$ is $C_1$-$C_6$ alkyl, $C_2$-$C_6$ alkenyl, $C_2$-$C_6$ alkynyl, $C_3$-$C_6$ cycloalkyl, arylalkyl having a $C_5$-$C_{10}$ aryl moiety and an $C_1$-$C_6$ alkyl moiety, or $C_5$-$C_{10}$ aryl;
  sulfoxides of the formula $SOR^8$ where $R^8$ is the same as above;
  sulfones of the formula $SO_2R^8$ where $R^8$ is the same as above;
  nitrile;
  $C_1$-$C_6$ acyl;
  alkoxycarbonylamino (carbamoyl) of the formula $NHCO_2R^8$ where $R^8$ is the same as above;
  carboxylic acid, or an ester, amide, or salt thereof;
  aminomethyl of the formula $CH_2NR^9R^{10}$ where $R^9$ and $R^{10}$ may be the same or different, and may be hydrogen, $C_1$-$C_6$ alkyl, $C_2$-$C_6$ alkenyl, $C_2$-$C_6$ alkynyl, $C_2$-$C_6$ hydroxyalkyl, $C_2$-$C_6$ methoxyalkyl, $C_3$-$C_6$ cycloalkyl, or $C_5$-$C_{10}$ aryl, or $R^9$ and $R^{10}$ together may form a ring of 5 or 6 atoms, the ring atoms selected from the group consisting of N and C;
  carboxamides of the formula $CONR^9R^{10}$ where $R^9$ and $R^{10}$ are the same as above, or $C_2$-$C_{30}$ peptide conjugates thereof; and
  sulfonamides of the formula $SO_2NR^9R^{10}$ where $R^9$ and $R^{10}$ are the same as above;

G is carbon or nitrogen;
$R^1$ is hydrogen, halogen, or $C_1$-$C_4$ alkyl, $C_2$-$C_4$ alkenyl, $C_2$-$C_4$ alkynyl;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;
$R^6$ is selected from the group consisting of:
  hydrogen;
  $C_1$-$C_6$ alkyl, $C_2$-$C_6$ alkenyl, $C_2$-$C_6$ alkynyl;
  $C_3$-$C_6$ cycloalkyl;
  arylalkyl having $C_5$-$C_{10}$ aryl and $C_1$-$C_6$ alkyl moieties;
  alkoxyalkyl having $C_1$-$C_4$ alkoxy and $C_1$-$C_4$ alkyl moieties;
  $C_2$-$C_4$ cyanoalkyl;
  $C_2$-$C_4$ hydroxyalkyl;
  aminocarbonylalkyl having a $C_1$-$C_4$ alkyl moiety; and
  $R^{12}COR^{13}$, where $R^{12}$ is $C_1$-$C_4$ alkylene, and $R^{13}$ is $C_1$-$C_4$ alkyl or $C_1$-$C_4$ alkoxy or hydroxy,
or $R^6$ is

and Ar² is a 5 or 6-member carbocyclic or heterocyclic aromatic ring with atoms selected from the group consisting of carbon, nitrogen, oxygen and sulfur, and having on a carbon atom thereof a substituent X, wherein X is selected from the group consisting of a halogen (fluorine, bromine, chlorine, iodine), hydrogen, hydroxy and esters thereof, carboxy and esters thereof; carboxy C1-C4 alkyl and esters thereof; carboxylic acid, alkoxy, hydroxymethyl, and esters thereof; and amino, and carboxamides and sulfonamides thereof; and pharmaceutically acceptable salts thereof.

Unexpectedly, the above identified compounds that do not comprise a phenolic ring substituted with a hydroxyl group or methylation of the hydroxyl group have been found to be effective for treatment of urinary tract problems even if light of the fact that phenol ring substituted with a hydroxyl group has been cited as a key pharmacophore for peptide and nonpeptide ligands to recognize delta-opioid receptors and produce physiological effects. Liao, et al. (1998), *J. Med. Chem.,* 41, 4767-4776.

In a further aspect of the invention, a pharmaceutical composition is provided for carrying out the methods of the invention. The pharmaceutical composition in one embodiment comprises an effective amount of at least one delta opioid receptor agonist selected from the group consisting of:

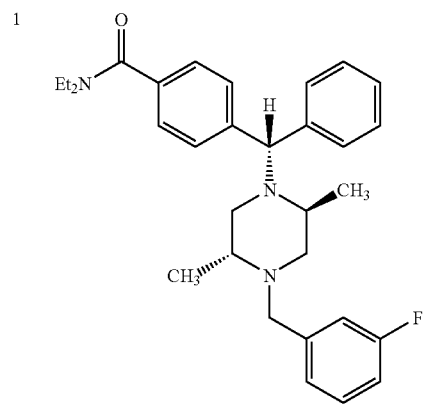

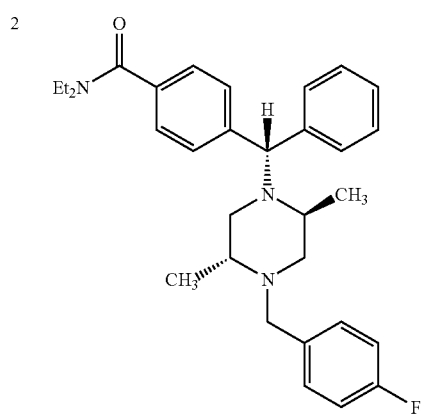

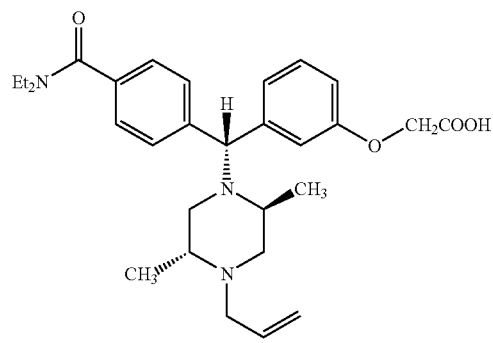

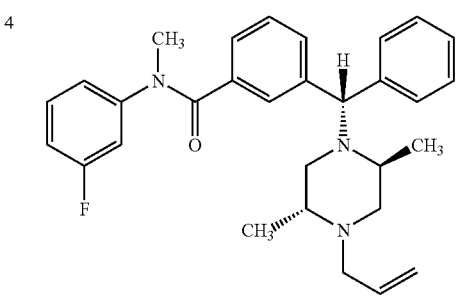

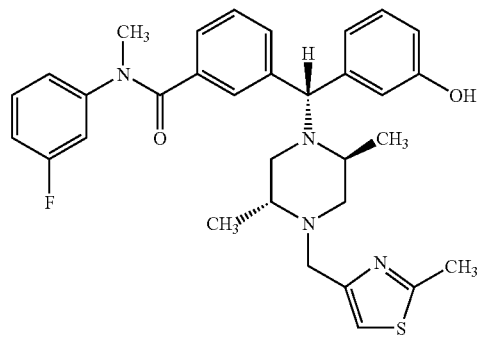

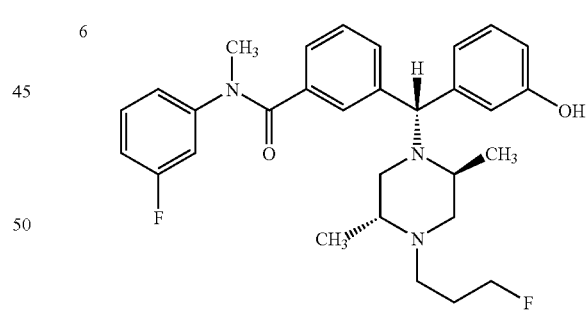

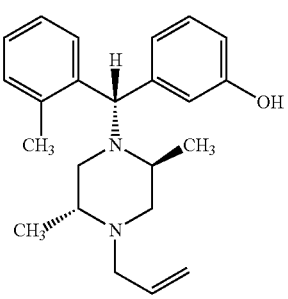

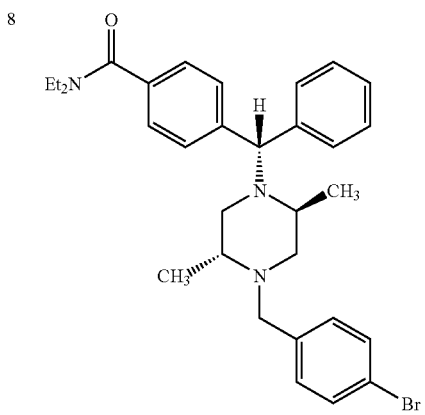

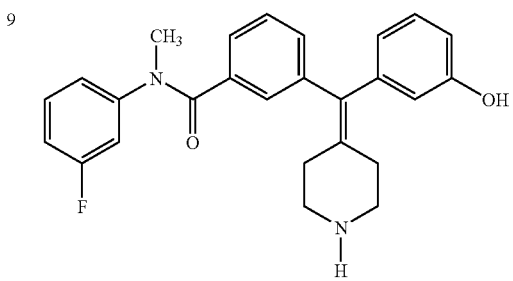

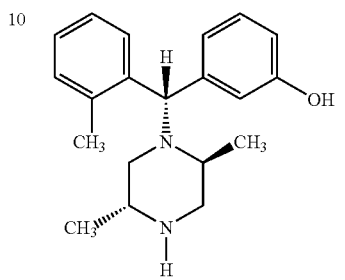

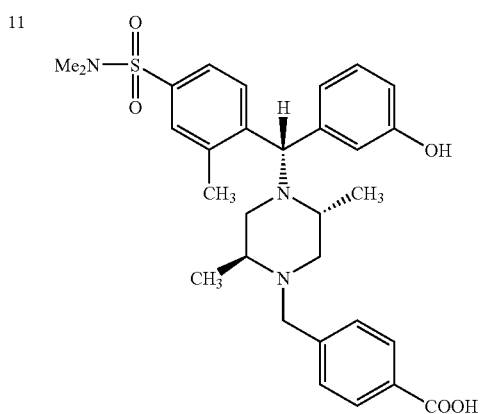

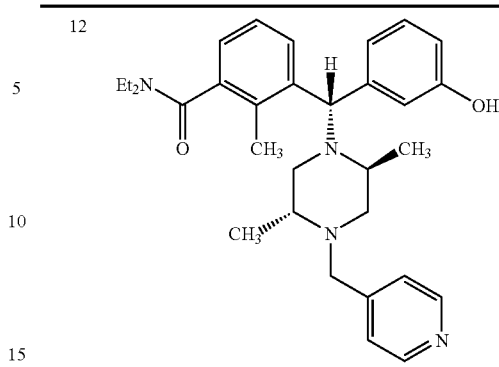

and pharmaceutically acceptable salts and esters thereof, in combination with a pharmacologically acceptable carrier, and optionally an additional active agent used for urinary dysfunction. The additional active agent may include, but is not limited to: alpha-adrenergic agonists, such as phenylpropanolamine and pseudoephedrein; anticholinergics, such as oxybutynin, propantheline, dicyclomine and tolterodine; alpha-adrenergic antagonists, such as prazosin, terazosin and doxazosin; and tricyclic antidepressants.

Other types of components may be incorporated in the composition as well, e.g., excipients, surfactants, preservatives, stabilizers, chelating agents and the like, as will be appreciated by those skilled in the art of pharmaceutical composition preparation and drug delivery.

Administration of the pharmaceutical composition is carried out within the context of a predetermined dosing regime such that the delta opioid receptor agonist is effective in the treatment of lower urinary tract dysfunction.

Delivery of the pharmaceutical compositions may be accomplished through any administrative route effective to provide relief from the urinary tract dysfunction, including, without limitation, oral, rectal, vaginal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, transurethral, intracavemosal injection and urethral suppository administration.

Yet another aspect of the present invention relates to a kit for treating a urinary tract dysfunction, e.g., enuresis, incontinence or dysuria, wherein the kit comprises a delta opioid receptor agonist as disclosed herein, e.g., in a pharmaceutically acceptable salt or ester form, wherein the opioid receptor agonist is provided in an amount effective to reduce the effect of the urinary tract dysfunction. The kit may also include written instructions with respect to administration, dosing frequency, contraindications for observance by the patient, etc., in a kit container such as a carrying and/or storage case.

Various other aspects, features and embodiments of the invention will be more fully apparent from the ensuing disclosure and appended claims.

BRIEF DESCRIPTION OF THE DRAWINGS

FIG. 1 summarizes the delta opioid receptor affinity of illustrative delta opioid receptor agonists of the present invention.

DETAILED DESCRIPTION OF THE INVENTION, AND PREFERRED EMBODIMENTS THEREOF

Figure 2B:
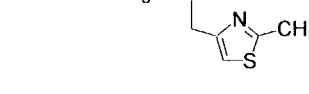
FIG. 2 summarizes the results of cystometric evaluation of two urodynamic parameters for illustrative delta opioid receptor agonists of the present invention administered by intravenous injection.
Figure 2B:
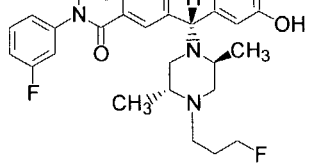
Figure 2B:
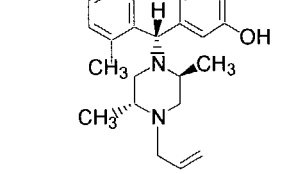
Figure 2B:
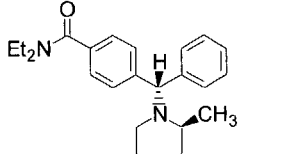
Figure 2B:
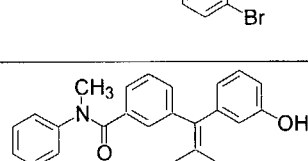
Figure 2B:
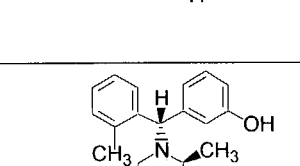

The disclosures of the following U.S. patents are hereby incorporated herein by reference, in their respective entireties:

Chang et al. U.S. Pat. No. 5,552,404 issued Sep. 3, 1996;
Chang et al. U.S. Pat. No. 5,574,159 issued Nov. 12, 1996;
Chang et al. U.S. Pat. No. 5,658,908 issued Aug. 19, 1997;
Chang et al. U.S. Pat. No. 5,681,830 issued Oct. 28, 1997;
Chang et al. U.S. Pat. No. 5,854,249 issued Dec. 29, 1998;
Chang et al. U.S. Pat. No. 5,807,858 issued Sep. 15, 1998;
Chang et al. U.S. Pat. No. 5,985,880 issued Nov. 16, 1999; and
Chang et al. U.S. Pat. No. 6,300,332 issued Oct. 9, 2001.

Delta opioid receptors are present in the central and peripheral nervous systems of many species including man. Delta opioid receptors have been identified as having a role in many bodily functions, such as circulatory and pain systems, immunomodulatory activities and gastrointestinal disorders.

Agonists are agents that recognize and bind to delta opioid receptors thereby affecting biochemical and/or physiological pathways by eliciting a pharmacological response. One of the major neuronal effects of opioid receptor activation is blocking the release and liberation of neurotransmitters, such as acetylcholine and norepinephine. While not wishing to be bound by any specific mechanism of action, it is believed that the activation of the delta opioid receptor with one of the specific delta opioid receptor agonists disclosed in the present invention ultimately leads to the inhibition of the release of acetylcholine from parasympathetic nerve endings, and consequently prevents smooth muscle from contracting with a concomitant delay of urination.

Definitions

Before describing the present invention in detail, it is to be understood that this invention is not limited to particular drug delivery systems. It is also to be understood that the terminology used herein is for the purpose of describing particular embodiments only, and is not intended to be limiting.

In describing and claiming the present invention, the following terminology will be used in accordance with the definitions set out below.

"Transdermal" delivery, as used herein includes transdermal (or "percutaneous") as well as transmucosal administration, i.e., delivery by passage of a drug through the skin or mucosal tissue and into the bloodstream.

"Topical administration" as used herein means delivery of a topical drug or pharmacologically active agent to the skin or mucosa.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

"Effective amount" of the compound for treating a urinary disorder as used herein is an amount that results in measurable amelioration of at least one symptom or parameter of the disorder.

Delta Opioid Receptor Agonists for Treating Urinary Dysfunction

In the method of the present invention, an effective amount of a delta opioid receptor agonist is administered to a subject experiencing or susceptible to urinary dysfunction. In a first embodiment, suitable delta opioid receptor agonists include the following compounds:

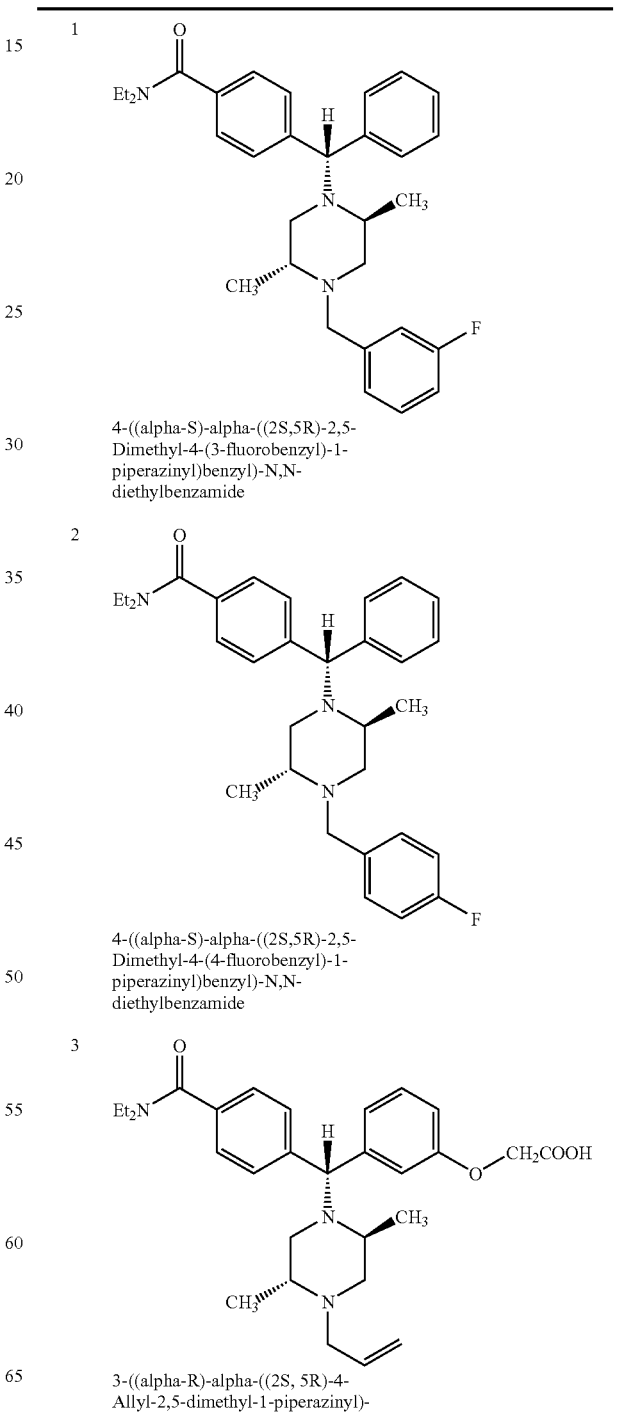

1  4-((alpha-S)-alpha-((2S,5R)-2,5-Dimethyl-4-(3-fluorobenzyl)-1-piperazinyl)benzyl)-N,N-diethylbenzamide 2  4-((alpha-S)-alpha-((2S,5R)-2,5-Dimethyl-4-(4-fluorobenzyl)-1-piperazinyl)benzyl)-N,N-diethylbenzamide 3  3-((alpha-R)-alpha-((2S, 5R)-4-Allyl-2,5-dimethyl-1-piperazinyl)-

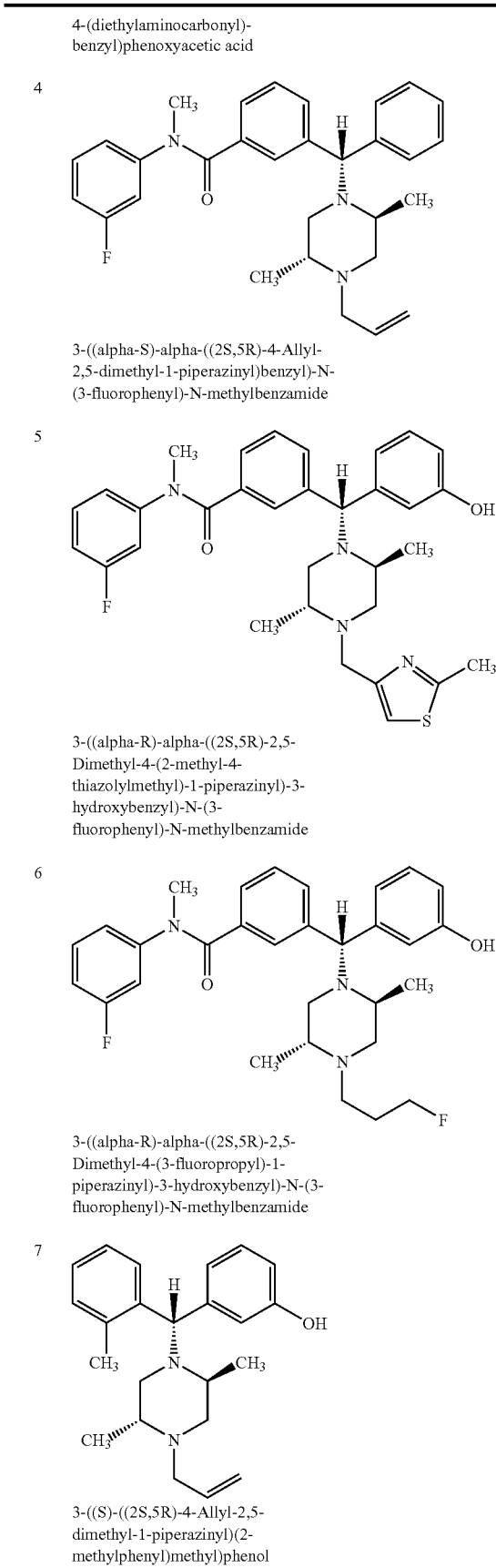
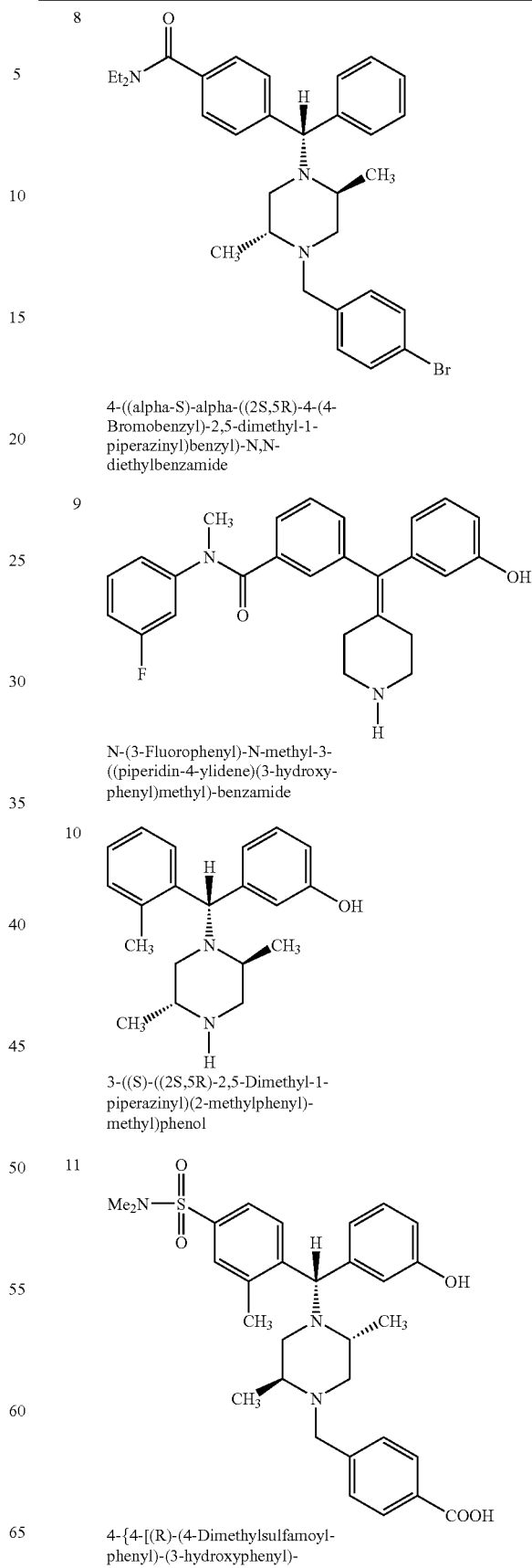

methyl]-(2S,5R)-dimethyl-
piperazin-1-ylmethyl}-benzoic
acid

12

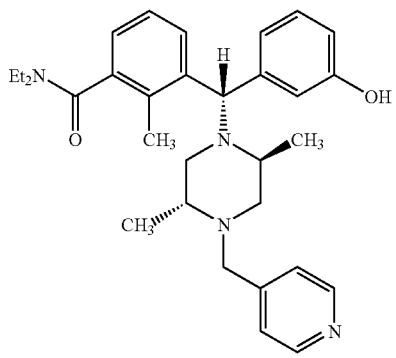

N,N-Diethyl-3-((R)-((2S,5R)-2,5-
dimethyl-4-(pyridin-4-yl-
methyl)piperazin-1-yl)(3-
hydroxyphenyl)methyl)benzamide as well as pharmaceutically acceptable salts, esters and active metabolites thereof. Combinations of such compounds are also contemplated for use within the scope of the present invention.

The delta opioid receptor agonist also may be administered in the form of an amide or prodrug and/or combination thereof. Salts, esters, amides and prodrugs of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base (typically wherein the neutral form of the drug has a neutral —$NH_2$ group) using conventional means, involving reaction with a suitable acid. Generally, the base form of the active agent is dissolved in a polar organic solvent, such as for example methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Examples of pharmaceutically acceptable salts include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl). Pharmaceutically acceptable salts of an amino group include salts of: organic carboxylic acids, such as acetic, lactic, tartaric, malic, lactobionic, fumaric, and succinic acids; organic sulfonic acids, such as methanesulfonic, ethanesulfonic, isethionic, benzenesulfonic and p-toluenesulfonic acids; and inorganic acids, such as hydrochloric, hydrobromic, sulfuric, phosphoric and sulfamic acids. Pharmaceutically acceptable salts of a compound having a hydroxyl group consist of the anion of such compound in combination with a suitable cation such as $Na^+$, $NH_4{}^+$, or $NR'_4{}^+$ (wherein R' is for example a $C_{1-4}$ alkyl group).

Preparation of esters involves functionalization of hydroxyl and/or carboxyl groups that may be present within the molecular structure of the delta opioid receptor agonist. The esters of hydroxyl groups are typically acyl-substituted derivatives of free alcohol groups, i.e., moieties that are derived from carboxylic acids of the formula RCOOH, where R is alkyl, and preferably is lower alkyl. Esters can be reconverted to the free acids, if desired, by using conventional hydrolysis procedures. Examples of pharmaceutically acceptable esters include carboxylic acid esters of the hydroxyl group in compounds of the present invention in which the non-carbonyl moiety of the carboxylic acid portion of the ester grouping is selected from straight or branched chain alkyl (e.g., n-propyl, t-butyl, n-butyl), alkoxyalkyl (e.g., methoxymethyl), arylalkyl (e.g., benzyl), aryloxyalky (e.g., phenoxymethyl), and aryl (e.g., phenyl); alkyl-, aryl-, or arylalkylsulfonyl (e.g., methanesulfonyl); amino acid esters (e.g., L-valyl or L-isoleucyl); dicarboxylic acid esters (e.g., hemisuccinate); carbonate esters (e.g., ethoxycarbonyl); carbamate esters (e.g., dimethylaminocarbonyl, (2-aminoethyl)aminocarbonyl); and inorganic esters (e.g., mono-, di- or triphosphate). The esters of carboxyl groups within the molecular structure of the drug are typically prepared from $C_1$-$C_4$ alcohols (e.g., ethanol, propanol) or arylalkyl alcohols (e.g., benzyl alcohols). Preparation of amides and prodrugs can be carried out in an analogous manner.

Other derivatives and analogs of the delta opioid receptor agonist may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Pharmaceutical Formulations and Modes of Administration:

Formulations of the present invention include those suitable for oral, nasal, topical (including buccal and sublingual), rectal, vaginal and/or parenteral administration. Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions include an effective amount of the delta opioid receptor agonist in combination with a pharmaceutically acceptable carrier, if desired, and, in addition, may include other pharmaceutical agents, adjuvants, diluents, buffers, etc. The amount of active agent administered will, of course, be dependent on the subject being treated, the subject's weight, the manner of administration and the judgment of the prescribing physician.

Urinary tract disorders and symptoms thereof include urgency, frequency, incontinence, urine leakage, enuresis, dysuria, hesitancy and difficulty emptying bladder. An additional parameter is the volume of urine. An effective amount of the delta opioid receptor agonist for treating the disorder can be determined by experimentation known in the art, such as by establishing a matrix of dosages and frequencies and comparing a group of experimental units or subjects to each point in the matrix. It will be understood that any clinically or statistically significant attenuation of any symptom or adverse aspect is within the scope of the invention. Clinically significant attenuation means perceptible to the patient and/or to the physician.

A single patient may suffer from several symptoms of dysuria simultaneously, such as urgency and frequency, either or both of which may be reduced using the methods of the present invention. In the case of incontinence, any reduction in the frequency or volume of unwanted passage of urine is considered a beneficial effect of the present methods of treatment.

The amount of the delta opioid receptor agonist that may be combined with a carrier material to produce a single dosage form preferably will be that amount effective to treat the urinary disorder. Generally, the amount of the delta opioid receptor agonist will range from about 1% to 99% by weight of the total formulation, preferably from about 5% to about 70%, and most preferably from about 10% to about 30%. The amount of delta opioid receptor agonist administered will further be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, or the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: the Science and Practice of Pharmacy, $19^{th}$ Ed. (Easton, Pa.: Mack Publishing Co., 1995).

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the delta receptor agonist of the present invention may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. Still another alternative approach for parenteral administration involves use of a slow release or sustained release system, such that a constant level of dosage is maintained.

The active agent can be administered in a pharmaceutical formulation suitable for transurethral drug delivery. The formulation contains one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

It may be desirable to deliver the compounds of the present invention in dosage form, which provides for controlled or sustained release of the delta opioid receptor agonist. In such a case, the dosage form typically comprises a biocompatible, biodegradable material, typically a biodegradable polymer. Examples of such polymers include polyester, polyalkylcyanoacrylate, polyorthoester, polyanhydride, albumin, gelatin and starch. These and other polymers can be used to provide biodegradable microparticles that enable controlled and sustained drug release, which in turn will minimize the required dosing frequency.

The compounds of the invention may also be delivered through the skin or muscosal tissue using conventional transdermal drug delivery systems, i.e., transdermal "patches" wherein a composition of the present invention is typically contained within a laminated structure that serves as a drug delivery device to be affixed to the body surface. In such a structure, the pharmaceutical composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the active agent-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

Alternatively, the pharmaceutical compositions of the invention may be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols. The weight of the suppository form will typically be in the range of approximately 1 mg to 50 mg. However, it will be appreciated by those skilled in the art that the size of the suppository can and will vary, depending on the potency of the active agent, the nature of the composition, and other factors.

The pharmaceutical compositions of the invention may also be administered by nasal aerosol or inhalation. Nasal spray formulations comprise purified aqueous solutions of the active compounds with preservative agents and isotonic agents. Such formulations are preferably adjusted to a pH and isotonic state compatible with the nasal mucous membranes. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

The delta opioid receptor agonists of the present invention may be prepared in formulations for topical drug delivery, such as in ointments and creams. Ointments are semisolid preparations that are typically based on petrolatum or other petroleum derivatives. Creams containing the selected delta opioid receptor agonist, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum delivery of the active agent. As with other carriers or vehicles, an ointment base should be inert, stable, nonirritating and nonsensitizing.

Ophthalmic formulations are prepared by a similar method to the nasal spray, except that the pH and isotonic factors are preferably adjusted to match that of the eye.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The pharmaceutical formulations discussed above may further contain one or more pharmacologically active agents in addition to a delta opioid receptor agonist of the present invention wherein the additional active agent is one that has been used to treat urinary tract dysfunctions and is administered in a lower dosage than normally administered without a delta opioid receptor agonist of the present invention, thereby alleviating or even eliminating the usual negative effects of the additional active agent. The additional pharmacologically active agent may include, but is not limited to, pseudoephedrine, ephedrine, phenylpropanolamine, prozosin, doxazosin, terazosin, antihistamines, tricyclic antidepressants, oxybutynin, propantheline, tolterodine, dicyclomine hydrochloride, indomethacin, baclofen, estrogens, imipramine, flavoxate, thiroidazine, haloperidol, benztropine, fluphenazine, terbutaline, propanolol, verapamil, methyldopa, reserpine, guanethidine and narcotics.

The delta opioid receptor agonists contemplated by the present invention include those illustratively described herein, as well as physiologically functional derivatives thereof. By "physiologically functional derivative" is meant a pharmaceutically acceptable salt, ether, ester or salt of an ether or ester of the compounds set forth above or any other compound which, upon administration to the recipient, is capable of providing (directly or indirectly) the said compound or an active metabolite or residue thereof.

The amount of delta opioid receptor agonist administered, and the dosing regimen used, will, of course, be dependent on the particular delta opioid receptor agonist selected, the age and general condition of the subject being treated, the severity of the subject's condition, and the judgment of the prescribing physician. In general, while the effective dosage of compounds of the invention for therapeutic use may be widely varied in the broad practice of the invention, depending on the specific condition involved, as readily determinable within the skill of the art, suitable therapeutic doses of the compounds of the invention, for each of the appertaining compositions described herein, and for achievement of therapeutic benefit in treatment of each of the conditions described herein, will preferably in the range of 10 micrograms (μg) to 500 milligrams (mg) per kilogram body weight of the recipient per day, more preferably in the range of 50 μg to 75 mg per kilogram body weight per day, and most preferably in the range of 1 mg to 50 mg per kilogram body weight per day. The desired dose once or as two, three, four, five, six, or more sub-doses administered at appropriate intervals throughout the day.

The mode of administration and dosage forms will of course affect the therapeutic amounts of the compounds which are desirable and efficacious for the given treatment application. For example, orally administered dosages typically are at least twice, e.g., 2-10 times, the dosage levels used in parenteral administration methods, for the same active ingredient. In oral administration, dosage levels for compounds of the present invention may be on the order of 5-200 mg/70 kg body weight/day. In tablet dosage forms, typical active agent dose levels are on the order of 10-100 mg per tablet.

Generally, the daily dosage when administered locally will be less than the dosage normally given in conjunction with systemic modes of administration, and typically, the delta opioid receptor agonist will be administered one to four times daily. Alternatively, a large initial loading dose can be used to achieve effective levels of the delta opioid receptor agonist and can be followed by smaller doses to maintain those levels. Depending on the half-life of the delta opioid receptor agonist and the availability via the chosen route of administration, the dosing regimen can be modulated in order to achieve satisfactory results in treating the urinary disorder.

Kits

The invention also encompasses a kit for patients to carry out the present method of treating lower urinary tract dysfunctions. The kit contains the pharmaceutical composition to be administered and/or a device for administering the pharmaceutical composition (e.g., a transurethral drug delivery device such as a syringe, a transdermal patch, etc.), a container, preferably sealed, for housing the composition and/or the delivery device during storage and prior to use, and instructions for carrying out drug administration in an effective manner. The formulation may consist of a delta opioid receptor agonist of the present invention in unit dosage form. The kit may contain multiple formulations of different dosages of the same agent. The instructions may be in written or pictographic form, or can be provided on recorded media including audio tape, video tape, or the like.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

The following examples are illustrative of synthetic procedures that may be advantageously utilized to make compounds of the present invention.

All chemical reagents were purchased from Aldrich Chemical Company, Milwaukee, Wis., unless otherwise specified. Commercial solvents were used without further purification. NMR spectra were obtained on a variety of instruments at field strengths ranging from 200 to 600 MHz. HPLC analyses were performed with a Waters liquid chromatography system equipped with a 717 plus Autosampler, 600E System Controller and a 996 Photodiode Array Detector. Mass spectra were performed by various contractual sources using chemical ionization (CI), electrospray (ES), or fast-atom bombardment (FAB) instrumentation. Analytical thin layer chromatography was performed on E. Merck glass plates pre-coated with silica gel GF (250 microns). Elemental analyses were performed by Atlantic Microlab, Norcross, Ga.

Example 1

4-((alpha-S)-alpha-((2S,5R)-2,5-Dimethyl-4-(3-fluorobenzyl)-1-piperazinyl)benzyl)-N,N-diethylbenzamide 4-Formyl-N,N-diethylbenzamide[4-(N,N-Diethylcarbamoyl)benzaldehyde]

4-Carboxybenzaldehyde (100.3 g, 0.67 mol) was dissolved/suspended in toluene (1200 mL), dimethylformamide (0.15 mL) was added and the suspension was stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue was dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M hydrochloric acid (2×600 mL), water (2×300 mL), dilute sodium carbonate solution (saturated:$H_2O$, 1:1, 2×600 mL), water (2×300 mL) and saturated sodium chloride solution (300 mL). The organic layer was separated, dried over anhydrous sodium sulfate, and evaporated to yield the title compound as a pale brown oil, which was used without further purification. (Yield 115.7 g, 84%).

4-((alpha-S)-alpha-((2S,5R)-4-Allyl-2,5-dimethyl-1-piperazinyl)benzyl)-N,N-diethyl benzamide A solution of 4-formyl-N,N-diethylbenzamide (51.3 g, 250 mmol), benzotriazole (29.8 g, 250 mmol) and (−)-(2R,5S)-1-allyl-2,5-dimethylpiperazine (38.6 g, 250 mmol, Chirotech Division of Dow Pharma, Cambridge, UK) in toluene (2500 mL) was heated under reflux under nitrogen with azeotropic removal of water for 2.5 h. Toluene was removed gradually via the Dean/Stark trap during this period until the residual volume of the reaction mixture was reduced to approximately 700-800 mL. The solution was diluted with anhydrous tetrahydrofuran (1000 mL), cooled to ~0° C. in an ice/isopropanol bath, and stirred under nitrogen during the addition over ~20 min of phenylmagnesium bromide (1.0 M in tetrahydrofuran, 500 mL, 500 mmol) through a wide-bore double-tipped needle. During the addition a suspension of magnesium salts began to form almost immediately, but did not become sufficiently thick to preclude efficient stirring. Initially the suspension was a yellow ochre in color, which persisted until about two-thirds of the Grignard reagent had been added, when the color of the reaction mixture changed rapidly to a ruddy brown. The ice bath was removed and the suspension was stirred at ambient temperature for 1.5 h, then quenched with saturated aqueous ammonium chloride solution (125 mL). The yellow suspension was stirred for 30 min, and anhydrous magnesium chloride (125 g) was added. The suspension was stirred for a further hour and filtered. The filter cake was washed with tetrahydrofuran (400 mL), and the combined filtrate and washings evaporated to a thick brown oil. The residue was partitioned between ethyl acetate (2500 mL) and aqueous sodium hydroxide solution (1.0 M, 1000 mL). The organic layer was separated and washed successively with 1M NaOH (3×1000 mL), water (3×1200 mL) and saturated aqueous sodium chloride solution (750 mL). Ethyl acetate (75 mL) was added to the partially crystallizing suspension, yielding a thick slurry of light-colored crystals in a dark mother liquor. The suspension was filtered, and the solid was washed sparingly with cold ethyl acetate and dried under vacuum at room temperature to yield a slightly off-white solid (38.31 g). The dark filtrate and washings were evaporated to a dark oil, which again partially crystallized on standing. The residue was triturated with ethyl acetate (20 mL) and filtered to yield a second crop of pale yellow crystals (4.04 g). Total yield 42.35 g, (40.4%). $^1$H NMR (($CD_3$)$_2$SO, 500 MHz); δ 0.94 (d, J=6.2 Hz, 3H); 1.09 (d, J=6.2 Hz, 3H, partially obscured by br m, 6H); 1.80 (m, 1H); 2.09 (dd, J=11, 7 Hz, 1H); 2.50 (br m, 1H, partially obscured by DMSO); 2.72 (dd, J=11, 2.8 Hz, 1H); 2.84 (dd, J=14, 7 Hz, 1H); 3.16 (dd, J=14, 5.2 Hz, 1H); 3.28 (br m, 3H); 5.10 (s, 1H), overlapped by 5.09 (d, J=10.6 Hz, 1H); 5.16 (dd, J=17, 1.4 Hz, 1H); 5.79 (m, 1H); 7.28 (m, 5H); 7.38 (m, 2H); 7.42 (d, J=8 Hz, 2H).

4-((alpha-S)-alpha-((2S,5R)-2,5-Dimethyl-1-piperazinyl)benzyl)-N,N-diethylbenzamide A solution of bis(dibenzylidineacetone)palladium (1.438 g, 2.5 mmol, Acros Organics) and 1,4-bis(diphenylphosphino)butane (1.066 g, 2.5 mmol, Acros Organics) in tetrahydrofuran (20 mL) was stirred under nitrogen at room temperature for 15 min, then added via syringe to a stirred solution under nitrogen of 4-((alpha-S)-alpha-((2S,5R)-4-allyl-2,5-dimethyl-1-piperazinyl)benzyl)-N,N-diethylbenzamide (20.98 g, 50 mmol) and thiosalicylic acid (9.25 g, 60 mmol) in anhydrous tetrahydrofuran (100 mL). The reaction mixture was stirred under nitrogen for 2 h at room temperature, evaporated to dryness, the residue dissolved in ethyl acetate (120 mL) and diluted with ether (300 mL). The solution was washed with dilute sodium carbonate solution (saturated:$H_2O$, 1:3, 3×200 mL). The organic solution was diluted with pentane (800 mL) and extracted with 3M hydrochloric acid (5×40 mL), followed by 1 M hydrochloric acid (3×50 mL, alternating with water (3×50 mL)). The combined aqueous extracts were filtered to remove a small amount of suspended solid and the pH adjusted to 12 with 5 M NaOH. The resulting oily suspension was extracted with methylene chloride (3×150 mL). The combined organic extracts were dried over anhydrous sodium sulfate and evaporated to dryness to yield 4-((alpha-S)-alpha-((2S,5R)-2,5-dimethyl-1-piperazinyl) benzyl)-N,N-diethylbenzamide as a very pale yellow solid (18.07 g, 97.8%) The product showed a single spot on thin layer chromatography (silica gel, EM60F$_{254}$, 4% NH$_4$OH/ 10% EtOH in ethyl acetate, R$_f$=0.25). and was used without further purification. Calc. for C$_{24}$H$_{33}$N$_3$O 0.2 H$_2$O: C, 75.24; H, 8.79; N, 10.97. Found C, 75.24; H, 8.87; N, 10.86%. $^1$H NMR (CDCl$_3$, 600 MHz); δ 0.93 (d, J=6.3 Hz, 3H); 1.12 (br m, 3H); 1.20 (d, J=6.1 Hz, 3H); 1.24 (br m, 3H); 1.55 (dd, J=9.7, 11.3 Hz, 1H, partially obscured by br m, 2H); 2.33 (m, 1H); 2.68 (m, 2H); 2.89 (m, 1H); 2.92 (dd, J=12.1, 3.1 Hz, 1H); 3.29 (br m, 2H); 3.54 (br m, 2H); 5.38 (s, 1H); 7.14 (m, 2H); 7.30 (m, 3H); 7.35 (m, 2H); 7.46 (d, J=7.8 Hz, 2H).

4-((alpha-S)-alpha-((2S,5R)-2,5-Dimethyl-4-(3-fluorobenzyl)-1-piperazinyl)benzyl)-N,N-diethylbenzamide A solution of 4-((alpha-S)-alpha-((2S,5R)-2,5-dimethyl-1-piperazinyl)benzyl)-N,N-diethylbenzamide (9.128 g, 24.05 mmol) in acetonitrile (150 mL) was added to sodium iodide (360 mg, 2.4 mmol) and stirred under nitrogen during the addition of triethylamine (12 mL, 8.76 g, 86.6 mmol), followed by 3-fluorobenzyl bromide (5.9 mL, 9.09 g, 48.1 mmol). An immediate turbidity was observed on addition of the fluorobenzyl bromide, thickening to a white crystalline precipitate over one hour. The reaction mixture was stirred under nitrogen overnight at room temperature. The solvent was removed by evaporation, and saturated sodium bicarbonate solution (25 mL) was added to the residue. The copious white precipitate was collected by filtration, washed well with water and dried under vacuum at room temperature. (10.54 g, 89.2%). Calc. for C$_{31}$H$_{38}$FN$_3$O 0.2 H$_2$O: C, 75.79; H, 7.88; N, 8.55; F, 3.87. Found C, 75.80; H, 7.78; N, 8.49; F, 3.75%.

The product was recrystallized by dissolving with stirring in hot isopropanol (39 mL) and heating to a gentle boil in a 250 mL Erlenmeyer flask. Water was added in portions until a permanent turbidity was observed in the gently boiling solution (22 mL water added). The flask was cooled to room temperature with stirring, and then was cooled in an ice-water bath with continued stirring for a further 1 h. The crystals were collected by filtration, washing with cold 2:1 isopropanol/water, to give white crystals (10.11 g, 96%). Calc. for C$_{31}$H$_{38}$FN$_3$O: C, 76.35; H, 7.85; N, 8.62; F, 3.90. Found C, 76.36; H, 7.85; N, 8.62; F, 3.77%. $^1$H NMR (CDCl3, 300 MHz); δ 1.06 (d, J=6.1 Hz, 3H); 1.15 (d, J=6.1 Hz, 3H, partially overlapped by br m, 3H); 1.22 (br m, 3H); 1.94 (dd, J=10.8, 8.1 Hz, 1H); 2.02 (dd, J=10.7, 8.2 Hz, 1H); 2.57 (br m, 2H); 2.67 (m, 2H); 3.18 (d, J=13.8 Hz, 1H); 3.28 (br m, 2H); 3.53 (br m, 2H); 3.87 (d, J=13.5 Hz, 1H); 5.15 (s, 1H); 6.90 (br t, J=8.2 Hz, 1H); 7.04 (m, 2H); 7.21 (m, 3H); 7.30 (m, 5H); 7.46 (d, J=8.0 Hz, 2H).

Example 2

4-((alpha-S)-alpha-((2S,5R)-2,5-Dimethyl-4-(4-fluorobenzyl)-1-piperazinyl)benzyl)-N,N-diethylbenzamide was prepared from 4-((alpha-S)-alpha-((2S,5R)-2,5-dimethyl-1-piperazinyl)benzyl)-N,N-diethylbenzamide (Example 1) and 4-fluorobenzyl bromide by a procedure similar to that described in Example 1. Calc. for C$_{31}$H$_{38}$FN$_3$O: C, 76.35; H, 7.85; N, 8.62; F, 3.90. Found C, 76.32; H, 7.86; N, 8.60; F, 3.95% $^1$H NMR (CDCl3, 600 MHz); δ 1.07 (d, J=6.2 Hz, 3H); 1.10 (d, J=6.3 Hz, 3H, partially overlapped by br m, 3H); 1.23 (br m, 3H); 1.93 (m, 1H); 1.98 (dd, J=11.1, 8.3 Hz, 1H); 2.54 (br m, 2H); 2.65 (m, 2H); 3.14 (d, J=13.1 Hz, 1H); 3.28 (br m, 2H); 3.54 (br m, 2H); 3.86 (d, J=13.1 Hz, 1H); 5.15 (s, 1H); 6.90 (t, J=8.2 Hz, 2H); 7.20 (d, J=7.3 Hz, 2H); 7.24 (m, 2H); 7.27 (m, 1H; partially overlapped by CHCl$_3$); 7.29 (d, J=9.4 Hz, 2H); 7.33 (m, 2H); 7.46 (d, J=8.1 Hz, 2H).

Example 3

3-((alpha-R)-alpha-((2S,5R)-4-Allyl-2,5-dimethyl-1-piperazinyl)-4-(diethylamino carbonyl)benzyl)phenoxyacetic acid A solution of 3-bromophenol (400 g, 2.31 mol), tert-butyl-chlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230-400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture 3-bromophenoxy-tert-butyldimethylsilane (27.3 g, 92.6 mmol) and dibromoethane (3.45 g, 18.4 mmol) in 100 mL of inhibitor-free anhydrous tetrahydrofuran to a solution of magnesium turnings (3.57 g, 147 mmol) in 200 mL of inhibitor-free anhydrous tetrahydrofuran at reflux. After stirring for one hour at reflux the light brown clear mixture was cooled to room temperature.

4-Carboxybenzaldehyde (100.3 g, 0.67 mol) was dissolved/suspended in toluene (1200 mL, dimethylformamide (0.15 mL) added and the suspension stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water 2×300 mL), dilute sodium carbonate solution (saturated: H$_2$O, 1:1, 2×600 mL), water (2×300 mL) and saturated sodium chloride solution (300 mL). The organic layer was separated, dried over anhydrous sodium sulfate and evaporated to yield 4-formyl-N,N-diethylbenzamide as a pale brown oil, which was used without further purification. (Yield 115.7 g, 84%)

In a 1000 mL round bottom flask fitted with a condenser and Dean-Stark trap were combined 4-formyl-N,N-diethylbenzamide (9.50 g, 46.3 mmol), benzotriazole (5.51 g, 46.3 mmol), and (2R,5S)-1-allyl-2,5-dimethylpiperazine (7.15 g, 46.3 mmol, Chirotech Division of Dow Pharma, Cambridge, England) with 400 mL of toluene. The reaction was heated to reflux under nitrogen until no additional water was observed in the trap (ca. 2 hours). The reaction was cooled to room temperature and concentrated under vacuum to leave a volume of approximately 50 mL. Anhydrous tetrahydrofuran (100 mL) was added to the flask under nitrogen with stirring to dissolve all residue. The solution of benzotriazole adduct was added to the solution of 3-tert-butyldimethylsilyloxyphenylmagnesium bromide (above) at room temperature via double-ended needle. After stirring for 2 hours, the reaction was quenched by addition of 20 mL of saturated aqueous ammonium chloride. Anhydrous magnesium sulfate was added and the reaction was filtered. Solvent was removed under vacuum and the residue was redissolved in 800 mL of ethyl acetate. The ethyl acetate solution was washed with 4×200 mL of 1 M sodium hydroxide, 200 mL of water, and 200 mL of saturated aqueous sodium chloride. The organic layer was dried over anhydrous magnesium sulfate and the solvent was removed to give 32.7 g of dark oil. The oil was dissolved in 250 mL of tetrahydrofuran and 250 mL of 3 M hydrochloric acid and stirred for 2 hours at room temperature. The reaction solution was extracted with 3×250 mL of 2:1 diethyl ether/ethyl acetate. Ethyl acetate (300 mL) was added to the aqueous layer and pH was adjusted to 8 with aqueous sodium hydroxide. Layers were separated and the aqueous portion was extracted with another 3×300 mL of ethyl acetate. The combined organic extracts were washed with saturated aqueous sodium chloride, dried over anhydrous sodium sulfate, and the solvent was removed under vacuum to give 12.4 g of brown residue. The residue was purified by chromatography on 300 g of silica gel, eluting with a gradient of 1-15% ethanol in dichloromethane, to give 5.54 g of 4-((alpha-R)-alpha-((2S,5R)-4-allyl-2,5-dimethyl-1-piperazinyl)-3-hydroxybenzyl)-N,N-diethylbenzamide as a colorless gum (27% from 4-formyl-N,N-diethylbenzamide).

Sodium hydride (60% dispersion in oil, 250 mg (150 mg NaH, 6.25 mmol)) was washed with anhydrous tetrahydrofuran (2×5 mL) and anhydrous tetrahydrofuran (10 mL) was added as supernatant. 4-((alpha-R)-alpha-((2S,5R)-4-Allyl-2,5-Dimethyl-1-piperazinyl)-3-hydroxybenzyl)-N,N-diethylbenzamide (435 mg, 1.0 mmol) was dissolved in the stirred suspension, and when effervescence had subsided, sodium iodide (15 mg, 0.1 mmol) was added. Methyl chloroacetate (350 mL, 434 mg, 4 mmol) was added to the stirred suspension under nitrogen and the reaction was stirred overnight at ambient temperature. The reaction mixture was partially neutralized by the passage of carbon dioxide gas (from dry ice), then glacial acetic acid added until the suspension showed a pH of 5 as measured by moistened indicator strips. The reaction mixture was evaporated to dryness, and the residue partitioned between ethyl acetate (10 mL) and 1 M HCl (5 mL). The organic layer was extracted with 1 M HCl (2×3 mL) and the pH of the combined acidic extracts was adjusted to 8 with saturated sodium carbonate solution. The oily aqueous suspension was extracted with ethyl acetate (3×10 mL) and the combined organic extracts were dried over anhydrous sodium sulfate. The solution was evaporated to a yellow gum. The residue was dissolved in ethyl acetate and applied to an intermediate (4×15 cm) silica gel Biotage column and eluted with 10% ethanol in ethyl acetate. Fractions containing the product, as evidenced by t.l.c. (silica, EM60F$_{254}$, 10% EtOH in EtOAc, Rf=0.52) were evaporated to dryness and dried at room temperature and 2 mm Hg to yield methyl 3-((alpha-R)-alpha-((2S,5R)-4-allyl-2,5-dimethyl-1-piperazinyl)-4-(diethylaminocarbonyl)benzyl)phenoxyacetate as a clear pale yellow gum. The residue was dissolved in ethanol (4 mL) and aqueous sodium hydroxide solution (2.5 M, 1.0 mL, 2.5 mmol) and stirred at room temperature for 6 h. The solution was evaporated to remove the bulk of the ethanol, and water (5 mL) was added. Evaporation was continued until approximately 4 mL of solution remained. A further 8 mL of water was added, and the solution was evaporated to approximately half its volume to ensure complete removal of ethanol. A small amount of suspended solid was removed by filtration, and the pH of the solution was adjusted to 6 with 3 M HCl. The solution was evaporated to dryness and the residue evaporated several times with absolute ethanol to ensure removal of water. The residue was extracted with ethanol (3×20 mL) and the combined ethanol extracts were filtered and evaporated to dryness. The gummy residue was triturated with ethyl acetate (5 mL), filtered, evaporated, and dried under high vacuum to yield 3-((alpha-R)-alpha-((2S,5R)-4-allyl-2,5-dimethyl-1-piperazinyl)-4-(diethylaminocarbonyl)benzyl)phenoxyacetic acid as a brittle white foam (52 mg, 9.5%). Calc. for $C_{29}H_{39}N_3O_4$ 0.9 NaCl 0.5 $H_2O$: C, 63.45; H, 7.20; N, 7.65. Found C, 63.83; H, 7.19; N, 7.25% $^1$H NMR (0.1 M NaOD in $D_2O$, 300 MHz); δ 0.86 (d, J=6.3 Hz, 3H); 0.94 (t, J=7.1 Hz, 3H); 1.01 (d, J=6.1 Hz, 3H); 1.09 (t, J=7.2 Hz, 3H); 1.81 (t, J=11.3 Hz, 1H); 2.09 (t, J=11.2 Hz, 1H); 2.43 (m, 2H); 2.73 (m, 3H); 3.13 (q, J=7.1 Hz, 2H); 3.25 (dd, J=13.5, 5.8 Hz, 1H); 3.38 (q, J=7.2 Hz, 2H); 4.32 (s, 2H); 5.09 (s, 1H); 5.14 (d, J=7.8 Hz, 1H); 5.24 (s, 1H); 5.74 (m, 1H); 6.73 (s, 1H); 6.80 (s, 2H); 7.21 (m, 3H); 7.32 (d, J=8.2 Hz, 2H). Mass spectrum: (ESI-, −5 KV, MeOH); m/z: 493, (M+, 25%); 492.5, ((M−1)+, 100%).

Example 4

3-((alpha-S)-alpha-((2R,5S)-4-Allyl-2,5-dimethyl-1-piperazinyl)-benzyl)-N-(3-fluorophenyl)-N-methylbenzamide 3-Fluoro-N-methylaniline was prepared from 3-fluoroaniline using a modified reductive amination. First, 1-hydroxymethylbenzotriazole was prepared by adding 37% aqueous formaldehyde to benzotriazole at 40° C. in a 1:1 ratio, then cooling to room temperature to precipitate the product. After filtration the hydroxymethylbenzotriazole (125 g) was heated to reflux in toluene with 3-fluoroaniline (92.2 g). Water was removed azeotropically using a Dean-Stark trap. After three hours, the mixture was cooled to room temperature, then refrigerated for several hours to complete precipitation. The white crystalline solid was filtered off, yielding 174.2 g (86.6%) of 1-(3-fluoroanilino)methyl)-1H-benzotriazole.

1-(3-fluoroanilino)methyl)-1H-benzotriazole (173.9 g) was slurried in dry tetrahydrofuran. Sodium borohydride (32.5 g) was added portionwise to the mixture at room temperature. After addition was complete, the mixture was refluxed for 4 hours. The solution was then cooled, and poured slowly into 400 mL 5N HCl with ice. This was stirred for 1 hour at room temperature. The solution pH was then adjusted to 9-10 using 10N sodium hydroxide solution. The product was extracted using diethyl ether. The ether extracts were washed with 1N sodium hydroxide solution, then saturated sodium chloride solution. The organic phase was dried over sodium sulfate, filtered then evaporated under reduced pressure to yield 87.5 g (97%) of 3-fluoro-N-methylaniline as a colorless oil. [NMR (200 MHz, DMSO-$d_6$): δ 2.76 (s, 3H); 3.41 (br.s, 1H); 6.59-6.92 (m, 3H); 7.27 (q, J=8.0 Hz, 1H)]. In lieu of chromatography, the oil was dissolved in diethyl ether and precipitated with ethereal HCl while stirring vigorously. The white solid was filtered, rinsed with ether, and then recrystallized from hot ethanol:ethyl acetate/~1:30. This hydrochloride salt is more stable and easier to manipulate than the free base.

3-carboxybenzaldehyde (Fluka; 12.01 g, 80 mmol) was slurried in 80 mL of dry toluene and thionyl chloride (7 mL, 96 mmol) and 5 drops of DMF. A reflux condenser with a calcium sulfate drying tube attached was placed on the flask. The mixture was refluxed for 1 hour after the solution went clear, and then allowed to cool. The volatiles were removed on the rotovap. The residue was pumped on briefly on a vacuum pump.

The crude acid chloride was then dissolved in 150 mL of dry tetrahydrofuran, and cooled in an ice/water bath. N-methyl-3-fluoroaniline hydrochloride (13.05 g, 80.8 mmol) was added. Triethylamine (35 mL, 250 mmol) in 50 mL of dry tetrahydrofuran was then added dropwise via an addition funnel. The cloudy solution was allowed to warm to room temperature over 1 hour, and allowed to stir overnight. To remove the copious amount of precipitate, 100 mL of diethyl ether was added and the reaction mixture was filtered. After rinsing the salts with more ether, the solvents were removed under reduced pressure. The residue was extracted with ethyl acetate, washed with 1N HCl twice, then with water, sodium carbonate solution, and saturated NaCl solution. The organic layer was dried over sodium sulfate/magnesium sulfate, and the solvent removed by evaporation at reduced pressure. Crude N-(3-fluorophenyl)-3-formyl-N-methylbenzamide as a light golden oil was obtained, 19.92 g (96% unchromatographed yield) [NMR (300 MHz, DMSO-$d_6$): δ 3.38 (s, 3H); 6.94-7.02 (m, 2H); 7.18-7.29 (m, 2H); 7.46 (t, J=7.7 Hz, 1H) 7.55 (d, J=7.6 Hz, 1H); 7.81 (m, 2H); 9.90 (s, 1H)].

2R,5S-1-allyl-2,5-dimethylpiperazine (3.30 g, 21.4 mmol, Chirotech Division of Dow Pharma, Cambridge, England), benzotriazole (2.58 g, 21.6 mmol), and N-(3-fluorophenyl)-3-formyl-N-methylbenzamide (5.51 g, 21.4 mmol) were mixed in 175 mL dry toluene with one drop of triethylamine. The mixture was immersed in an oil bath maintained at 120-130° C. (bath temperature). The flask was attached to a Dean-Stark trap to allow the azeotropic removal of water. The mixture was refluxed for 2-3 hours under nitrogen, and ~150 mL of toluene/water azeotrope was collected. The remaining toluene was removed under reduced pressure. Due to the water-sensitive nature of the adduct, the amber/yellow-colored oil crude material was used for the subsequent reaction.

The crude benzotriazole adduct described above was dissolved in 100 mL tetrahydrofuran and added to 40 mL of 1M phenylmagnesium bromide in tetrahydrofuran (40 mmol) via a double-ended needle. The reaction was slightly exothermic and turned into a yellow-brown, cloudy solution. After stirring under nitrogen at room temperature for 2 hours, the reaction was quenched with 5 mL of saturated ammonium chloride solution. Having stirred this for about half an hour, a generous amount of anhydrous magnesium sulfate was added. Filtering and concentrating the solution under reduced pressure gave the crude product contaminated with benzotriazole. This residue was dissolved in 150 mL ethyl acetate and 100 mL diethyl ether, and extracted with 1M NaOH solution (4×100 mL) to remove the benzotriazole. The organic layer was extracted with 2N HCl solution (2×75 mL). The combined aqueous acidic extracts were adjusted to pH 2.5 with 25% aqueous NaOH solution, extracted with ethyl acetate (3×75 mL), and the aqueous portion discarded. The combined organic extracts was then adjusted to pH 9 with 1M NaOH solution and separated. After washing with saturated sodium chloride solution, drying over sodium sulfate/magnesium sulfate, the ethyl acetate was removed under reduced pressure. The residual oil was purified by chromatography on silica gel (EtOAc+2% $NH_4OH/CH_2Cl_2$) to give 2.03 g (4.3 mmol) of the desired product as an amber/orange resin. $^1$H NMR (300 MHz, $CDCl_3$): δ 7.10-7.38 (m, 8H), 6.97 (br dd, J~7.5 Hz, 2H), 6.83-6.89 (m, 1H), 6.76 (br d, J~7.8 Hz, 2H), 5.76-5.93 (m, 1H), 5.19 (d, J=12.6 Hz, 1H), 5.16 (d, J=5.4 Hz, 1H), 5.08 (s, 1H), 3.48 (s, 3H), 3.37 (dd, J=6.0, 14.4 Hz, 1H), 2.84 (dd, J=8.1, 8.1 Hz, 1H), 2.77 (dd, J=3.0, 11.4 Hz, 1H), 2.44-2.56 (m, 1H), 2.38 (br d, J~9.3 Hz, 2H), 2.06 (t, J=10.5 Hz, 1H), 1.67-1.80 (m, 2H), 1.10 (d, J=6.0 Hz, 3H), 0.96 (d, J=6.0 Hz, 3H).

Calculated for $C_{30}H_{34}FN_3O$. 0.25 $C_4H_8O_2$: C, 75.43; H, 7.35; N, 8.51; F, 3.85%. Found: C, 75.47; H, 7.38; N, 8.34; F, 3.70%. This material was converted to the hydrochloride salt and precipitated from $CH_2Cl_2/Et_2O$ as powdery, light tan solid. Calculated for $C_{30}H_{34}FN_3O$.2.0 HCl.0.3 $C_4H_{10}O$.0.03 $CH_2Cl_2$: C, 65.89; H, 6.92; N, 7.38; Cl, 12.83%. Found: C, 65.75; H, 7.03; N, 7.13; Cl, 12.76%.

Example 5

3-((alpha-R)-alpha-((2S,5R)-2,5-Dimethyl-4-(2-methyl-4-thiazolylmethyl)-1-piperazinyl)-3-hydroxybenzyl)-N-(3-fluorophenyl)-N-methylbenzamide 3-Fluoro-N-methylaniline was prepared from 3-fluoroaniline using a modified reductive amination. First, 1-hydroxymethylbenzotriazole was prepared by adding 37% aqueous formaldehyde to benzotriazole at 40° C. in a 1:1 ratio, then cooling to room temperature to precipitate the product. After filtration the hydroxymethylbenzotriazole (125 g) was heated to reflux in toluene with 3-fluoroaniline (92.2 g). Water was removed azeotropically using a Dean-Stark trap. After three hours, the mixture was cooled to room temperature, then refrigerated for several hours to complete precipitation. The white crystalline solid was filtered off, yielding 174.2 g (86.6%) of 1-(3-fluoroanilino)methyl)-1H-benzotriazole.

1-(3-Fluoroanilino)methyl)-1H-benzotriazole (173.9 g) was slurried in dry tetrahydrofuran. Sodium borohydride (32.5 g) was added portionwise to the mixture at room temperature. After addition was complete, the mixture was refluxed for 4 hours. The solution was then cooled, and poured slowly into 400 mL 5N HCl with ice. This was stirred for 1 hour at room temperature. The solution pH was then adjusted to 9-10 using 10N sodium hydroxide solution. The product was extracted using diethyl ether. The ether extracts were washed with 1N sodium hydroxide solution, then saturated sodium chloride solution. The organic phase was dried over sodium sulfate, filtered then evaporated under reduced pressure to yield 87.5 g (97%) of 3-fluoro-N-methylaniline as a colorless oil. [NMR (200 MHz, DMSO-$d_6$): δ 2.76 (s, 3H); 3.41 (br.s, 1H); 6.59-6.92 (m, 3H); 7.27 (q, J=8.0 Hz, 1H)]. In lieu of chromatography, the oil was dissolved in diethyl ether and precipitated with ethereal HCl while stirring vigorously. The white solid was filtered, rinsed with ether, and then recrystallized from hot ethanol:ethyl acetate/~1:30. This hydrochloride salt is more stable and easier to manipulate than the free base.

3-carboxybenzaldehyde (Fluka; 12.01 g, 80 mmol) was slurried in 80 mL of dry toluene and thionyl chloride (7 mL, 96 mmol) and 5 drops of DMF. A reflux condenser with a calcium sulfate drying tube attached was placed on the flask. The mixture was refluxed for 1 hour after the solution went clear, and then allowed to cool. The volatiles were removed on the rotovap. The residue was pumped on briefly on a vacuum pump. The crude acid chloride was then dissolved in 150 mL of dry tetrahydrofuran, and cooled in an ice/water bath. N-methyl-3-fluoroaniline hydrochloride (13.05 g, 80.8 mmol) was added. Triethylamine (35 mL, 250 mmol) in 50 mL of dry tetrahydrofuran was then added dropwise via an addition funnel. The cloudy solution was allowed to warm to room temperature over 1 hour, and allowed to stir overnight. To remove the copious amount of precipitate, 100 mL of diethyl ether was added and the reaction mixture was filtered. After rinsing the salts with more ether, the solvents were removed under reduced pressure. The residue was extracted with ethyl acetate, washed with 1N HCl twice, then with water, sodium carbonate solution, and saturated NaCl solution. The organic layer was dried over sodium sulfate/magnesium sulfate, and the solvent removed by evaporation at reduced pressure. Crude N-(3-fluorophenyl)-3-formyl-N-methylbenzamide as a light golden oil was obtained, 19.92 g (96% unchromatographed yield) [NMR (300 MHz, DMSO-$d_6$): δ 3.38 (s, 3H); 6.94-7.02 (m, 2H); 7.18-7.29 (m, 2H); 7.46 (t, J=7.7 Hz, 1H) 7.55 (d, J=7.6 Hz, 1H); 7.81 (m, 2H); 9.90 (s, 1H)].

2R,5S-1-Allyl-2,5-dimethylpiperazine (1.28 g, 8.3 mmol, Chirotech Division of Dow Pharma, Cambridge, England), benzotriazole (1.00 g, 8.3 mmol), and N-(3-fluorophenyl)-3-formyl-N-methylbenzamide (2.14 g, 8.3 mmol) were mixed in 100 mL dry toluene with one drop of triethylamine. The mixture was immersed in an oil bath maintained at 120-130° C. (bath temperature). The flask was attached to a Dean-Stark trap to allow the azeotropic removal of water. The mixture was refluxed for 2-3 hours under nitrogen, and ~75 mL of toluene/water azeotrope was collected. The remaining toluene was removed under reduced pressure. Due to the water-sensitive nature of the adduct, the amber/yellow-colored oil crude material was used for the subsequent reaction.

A solution of 3-bromophenol (8.65 g, 50 mmol), tert.-butylchlorodimethylsilane (7.97 g, 51.8 mmol), and imidazole (8.85 g, 130 mmol) in 70 mL of anhydrous dimethylformamide was stirred overnight at room temperature. After concentrating the reaction mixture under reduced pressure, the residue was dissolved in 200 mL of diethyl ether, extracted with 250 mL of water twice, and washed with saturated sodium chloride solution. The ether extract was dried over sodium sulfate/magnesium sulfate and the solvent removed under reduced pressure. The pale yellow liquid was chromatographed on a short column (3.5×10 cm) of silica gel, eluting with pentane. Combining the desired fractions and removing the solvent left 12.78 g (89%) of 3-(bromophenoxy)-tert.-butyldimethylsilane as a clear liquid. NMR (300 MHz, CDCl$_3$): δ 0.2 (s, 6H); 1.0 (s, 9H); 6.75 (m, 1H); 7.0 (br s, 1H); 7.1 (m, 2H).

A solution of 3-(bromophenoxy)-tert.-butyldimethylsilane (4.21 g, 14.6 mmol, 1.76 eq.) was dissolved in dry tetrahydrofuran (30 mL), and cooled to −75° C. under nitrogen. While this solution was stirring briskly, n-butyllithium in hexanes (9.1 mL of a 1.6M solution, 14.5 mmol, 1.75 eq.) was added slowly via a syringe to the solution. After stirring for 40 minutes at −75° C., the solution was transferred via a double-ended needle to a flask containing a suspension of magnesium bromide etherate (4.37 g, 16.9 mmol, 2.03 eq.) in anhydrous tetrahydrofuran (50 mL) and stirred for 1 hour at room temperature. Next, the crude benzotriazole adduct (formed with 2R,5S-1-allyl-2,5-dimethylpiperazine as described above) was dissolved in ~10 mL of tetrahydrofuran and added to the freshly prepared arylmagnesium bromide reagent via a double-ended needle. The reaction was slightly exothermic and turned into a yellow-brown, cloudy solution. After stirring under nitrogen at room temperature for 2 hours, the reaction was quenched with 3-4 mL of saturated ammonium chloride solution. Having stirred this for about half an hour, a generous amount of anhydrous magnesium sulfate was added. Filtering and concentrating the solution under reduced pressure gave the crude silyl ether contaminated with benzotriazole by-product. This residue was dissolved in ethyl acetate and extracted with 10% aqueous NaOH solution three times to remove most of the benzotriazole. The organic layer was washed with saturated sodium chloride solution, dried over sodium sulfate/magnesium sulfate, and the ethyl acetate was removed under reduced pressure.

The t-butyldimethylsilyl protecting group was removed by dissolving the residue in 40 mL of tetrahydrofuran and adding 40 mL of 3N aqueous HCl at room temperature. The solution warmed upon acid addition. The mixture was stirred for 90 minutes at room temperature. The reaction was concentrated under reduced pressure to remove most of the organic solvent. The residue was partitioned between water and a solution of diethyl ether:ethyl acetate/3:2. The acidic aqueous layer was extracted twice with a solution of diethyl ether:ethyl acetate/ 3:2. The aqueous layer was adjusted to pH=2 using aqueous NaOH solution, at which point cloudiness persisted and a dark oil began to precipitate. Methylene chloride (~100 mL) was added and stirred briskly. This was separated and the aqueous layer was again washed with more methylene chloride. The combined organic extract was partitioned with water, and while stirring vigorously was adjusted to pH=9 using aqueous NaOH solution. This was then separated and the aqueous layer was again washed with more methylene chloride. The combined extract was dried over sodium sulfate/magnesium sulfate, and the solvent was evaporated under reduced pressure. The crude material was chromatographed on silica gel column (roughly 20-25 g of silica gel per gram of crude material) eluting first with methylene chloride, then with 20% ethyl acetate in methylene chloride to remove the less polar contaminant. Then, the column was eluted with a solution of ethyl acetate containing 2% ammonium hydroxide (solution A) in a gradient with methylene chloride (solution B), quickly increasing in polarity from 25% to 100% (solution A in B). The desired fractions were combined and the solvent was removed under reduced pressure to give a 10:1 mixture of diastereomers in 60% crude yield.

The product was crystallized by dissolving the mixture of diastereomers in hot ethyl acetate (2-3 mL/g of material) and adding hexane (twice the volume of ethyl acetate), in portions, while keeping the solution hot. Allowing the solution to cool gradually with stirring for 24 hours gave 1.78 g of (+)-3-((alpha-R)-alpha-((2S,5R)-4-allyl-2,5-dimethyl-1-piperazinyl)-3-hydroxybenzyl)-N-(3-fluorophenyl)-N-methylbenzamide as an off-white crystalline solid (m.p.=144-145° C.). NMR (200 MHz, DMSO-$d_6$): δ 0.84 (d, J=6.0 Hz, 3H); 0.97 (d, J=5.9 Hz, 3H); 1.69 (dd, $J_1$=7.7 Hz, $J_2$=10.7 Hz, 1H); 2.01 (dd, $J_1$=7.4 Hz, $J_2$=10.7 Hz, 1H); 2.28 (br. d, J=8.3 Hz, 1H); 2.40-2.52 (m, 2H); 2.67 (br d, J=10.5 Hz, 1H); 2.82 (dd, $J_1$=7.6 Hz, $J_2$=13.2 Hz, 1H); 3.17 (br. d, J=14.0 Hz, 1H); 3.34 (s, 3H); 4.80 (s, 1H); 5.10 (d, J=10.1 Hz, 1H); 5.17 (d, J=17.3 Hz, 1H); 5.70-5.84 (m, 1H); 6.42 (d, J=7.1 Hz, 1H); 6.56 (s, 1H); 6.65 (d, J=8.3 Hz, 1H); 6.90-7.32 (m, 9H); 9.31 (s, 1H). Mass spectrum (CI—CH$_4$) m/z: 488 (m+1, 100%), 334 (39%), 153 (87%). $[α]_D^{20}$=+4.9° (abs. ethanol, c=1.2).

(+)-3-((alpha-R)-alpha-((2S,5R)-4-Allyl-2,5-dimethyl-1-piperazinyl)-3-hydroxybenzyl)-N-(3-fluorophenyl)-N-methylbenzamide (4.88 g, 10 mmol), N-phenyltrifluoromethane-sulfonimide (3.82 g, 10.7 mmol), and triethylamine (3.1 mL, 22 mmol) were dissolved in 75 mL dichloromethane and stirred overnight at room temperature under nitrogen. After concentrating under reduced pressure, the residue was dissolved in 100 mL ethyl acetate and washed with Na$_2$CO$_3$ solution (3×100 mL), water (1×100 mL), and brine (1×100 mL). The solution was dried (Na$_2$SO$_4$/MgSO$_4$) and concentrated under reduced pressure. The residual oil was purified by chromatography on silica gel (EtOAc+2% NH$_4$OH/CH$_2$Cl$_2$) to give 6.1 g (9.8 mmol) of the trifluoromethanesulfonate ester as a viscous, golden yellow oil.

The allyl portion was removed using Pd(dba)$_2$/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 50 mL ethyl acetate and 100 mL diethyl ether. After washing this with $Na_2CO_3$ solution (3×100 mL) and water (1×100 mL), the organic solution was extracted with 3 N HCl (3×20 mL) and 1 N HCl (1×20 mL). The acidic extract was adjusted to pH 8.5 using NaOH solution and extracted with dichloromethane (3×25 mL). The solution was dried ($Na_2SO_4/MgSO_4$) and concentrated under reduced pressure. The residual oil was purified by chromatography on silica gel (EtOAc+2% $NH_4OH/CH_2Cl_2$) to give 4.44 g (7.6 mmol) of 3-((alpha-R)-alpha-((2S,5R)-2,5-dimethyl-1-piperazinyl)-3-(trifluoromethylsulfonyloxy)benzyl)-N-(3-fluorophenyl)-N-methylbenzamide as a viscous, deep amber-orange colored oil.

The above free amine (0.93 g, 1.6 mmol) was combined with anhydrous sodium carbonate powder (1.39 g, 13.2 mmol), 10 mL anhydrous acetonitrile, sodium iodide (0.10 g, 0.67 mmol), and 4-chloromethyl-2-methylthiazole hydrochloride (0.34 g, 1.84 mmol). The reaction was stirred for two days at room temperature under nitrogen, and then concentrated under reduced pressure. The residue was suspended in 15 mL ethanol, 10 mL of 2N NaOH solution was added, and the reaction was stirred overnight at room temperature. The ethanol was removed under vacuum and the residue was partitioned between water and dichloromethane. The solution was adjusted to pH 8.5 using 6 N HCl, separated and extracted again with dichloromethane (2×25 mL). The solution was dried ($Na_2SO_4/MgSO_4$) and concentrated under reduced pressure. The residual oil was purified by chromatography on silica gel (EtOAc+2% $NH_4OH/CH_2Cl_2$) to give 0.71 g (1.2 mmol) of 3-((alpha-R)-alpha-((2S,5R)-2,5-dimethyl-4-(2-methyl-4-thiazolylmethyl)-1-piperazinyl)-3-hydroxybenzyl)-N-(3-fluorophenyl)-N-methylbenzamide as an off-white foam. $^1$H NMR (300 MHz, $d_6$-DMSO): δ 9.31 (s, 1H), 7.15-7.26 (m, 6H), 6.95-7.09 (m, 3H), 6.86 (d, J=7.9 Hz, 1H), 6.62 (dd, J=1.5, 8.0 Hz, 1H), 6.52 (s, 1H), 6.38 (d, J=7.5 Hz, 1H), 4.81 (s, 1H), 3.70 (d, J=14.5 Hz, 1H), 3.47 (d, J=14.5 Hz, 1H), 3.31 (s, 3H), 2.67 (br dd, J=~9 Hz, 1H), 2.60 (s, 3H), 2.37-2.48 (m, 2H—partially obscured by DMSO peak), 2.27 (br d, J=~9 Hz, 1H), 2.05 (dd, J=8.4, 10.9 Hz, 1H), 1.65 (dd, J=8.4, 10.9 Hz, 1H), 0.96 and 0.94 (overlapping pair d, J=~7 Hz, 3H). Calculated for $C_{32}H_{35}FN_4O_2S.0.30$ $C_4H_8O_2.0.07$ $CH_2Cl_2$: C, 67.60; H, 6.40; N, 9.48; F, 3.21; S, 5.42%. Found: C, 67.51; H, 6.54; N, 9.47; F, 3.22; S, 5.65%. This material was converted to the hydrochloride salt and lyophilized from EtOH/$H_2O$ as a fluffy, off-white solid. Calculated for $C_{32}H_{35}FN_4O_2S.1.0$ HCl.0.85 $H_2O$: C, 62.96; H, 6.22; N, 9.18; S, 5.25; Cl, 5.81%. Found: C, 63.06; H, 6.22; N, 8.99; S, 5.26; Cl, 5.85%.

Example 6

3-((alpha-R)-alpha-((2S,5R)-2,5-Dimethyl-4-(3-fluoropropyl)-1-piperazinyl)-3-hydroxybenzyl)-N-(3-fluorophenyl)-N-methylbenzamide 3-((alpha-R)-alpha-((2S,5R)-2,5-Dimethyl-1-piperazinyl)-3-(trifluoromethylsulfonyloxy)-benzyl)-N-(3-fluorophenyl)-N-methylbenzamide (from Example 5, 0.70 g, 1.2 mmol) was combined with anhydrous sodium carbonate powder (0.65 g, 6.1 mmol), 10 mL anhydrous acetonitrile, sodium iodide (0.03 g, 0.2 mmol), and 1-bromo-3-fluoropropane (0.12 mL, 1.3 mmol). The reaction was stirred for three days at room temperature under nitrogen, and then concentrated under reduced pressure. The residue was suspended in 15 mL ethanol, 10 mL of 10% w/v aqueous NaOH solution was added, and the reaction was stirred 2 hours at room temperature. The ethanol was removed under vacuum and the residue was partitioned between water and dichloromethane. The solution was adjusted to pH 8.5 using 3 N HCl, separated and extracted again with dichloromethane (2×15 mL). The solution was dried ($Na_2SO_4/MgSO_4$) and concentrated under reduced pressure. The residual oil was purified by chromatography on silica gel (EtOAc+2% $NH_4OH/CH_2Cl_2$) to give 0.39 g (0.77 mmol) of the desired product as an off-white foam. $^1$H NMR (600 MHz, $d_6$-DMSO): δ 9.28 (s, 1H), 7.17-7.24 (m, 5H), 7.04-7.07 (m, 2H), 6.97 (dt, J=2.2, 8.4 Hz, 1H), 6.88 (dd, J=1.2, 8.0 Hz, 1H), 6.61 (dd, J=1.8, 8.0 Hz, 1H), 6.55 (s, 1H), 6.41 (d, J=7.4 Hz, 1H), 4.74 (br s, 1H), 4.42 (dt, J=47.5, 6.0 Hz, 2H), 3.30 (s, 3H), 2.70 (dd, J=2.9, 11.0 Hz, 1H), 2.55-2.61 (m, 1H), 2.48-2.52 (m, 1H—partially obscured by DMSO peak), 2.38-2.42 (m, 1H), 2.26 (br d, J~9.2 Hz, 1H), 2.19-2.24 (m, 1H), 2.00 (dd, J=7.3, 10.8 Hz, 1H), 1.70-1.75 (m, 1H), 1.64-1.70 (m, 2H), 0.95 (d, J=6.2 Hz, 3H), 0.86 (d, J=6.2, Hz, 3H). Calculated for $C_{30}H_{35}F_2N_3O_2$: C, 70.98; H, 6.95; N, 8.28; F, 7.48%. Found: C, 70.78; H, 7.23; N, 8.19; F, 7.24%.

Example 7

3-((S)-((2S,5R)-4-Allyl-2,5-dimethyl-1-piperazinyl) (2-methylphenyl)methyl)phenol 2R,5S-1-allyl-2,5-dimethylpiperazine (3.06 g, 20 mmol, Chirotech Division of Dow Pharma, Cambridge, England), benzotriazole (2.38 g, 20 mmol), and 2-tolualdehyde (2.40 g, 20 mmol) were mixed in 140 mL dry toluene. The mixture was immersed in an oil bath maintained at 120-130° C. (bath temperature). The flask was attached to a Dean-Stark trap to allow the azeotropic removal of water. The mixture was refluxed for 2-2.5 hours under nitrogen, and ~100 mL of toluene/water azeotrope was collected. The remaining toluene was removed under reduced pressure. Due to the water-sensitive nature of the adduct, the crude amber/yellow-colored oil was used for the subsequent reaction without purification.

A solution of 3-(bromophenoxy)-tert.-butyldimethylsilane (from Example 5, 9.49 g., 33 mmol) was dissolved in dry tetrahydrofuran (50 mL), and cooled to −75° C. under nitrogen. While this solution was stirring briskly, n-butyllithium in hexanes (13 mL of a 2.5M solution, 32.5 mmol) was added slowly via a syringe to the solution. After stirring for 45 minutes at −75° C., the solution was transferred via a double-ended needle to a flask containing a suspension of magnesium bromide etherate (9.55 g, 37 mmol) in anhydrous tetrahydrofuran (100 mL) and stirred for 1 hour at room temperature. Next, the crude benzotriazole adduct (formed with 2R,5S-1-allyl-2,5-dimethylpiperazine and tolualdehyde, described above) was dissolved in ~50 mL of tetrahydrofuran and added over 5 minutes to the freshly prepared arylmagnesium bromide reagent via a double-ended needle. The reaction was slightly exothermic and turned into a yellow-brown, cloudy solution. After stirring under nitrogen at room temperature for 2 hours, the reaction was quenched with 5 mL of saturated ammonium chloride solution. Having stirred this for about 5 minutes, a generous amount of anhydrous magnesium sulfate was added. Filtering and concentrating the solution under reduced pressure gave the crude silyl ether contaminated with benzotriazole by-product. This residue was dissolved in ethyl acetate and extracted with 1N aqueous NaOH solution (3×100 mL) to remove most of the benzotriazole. The organic layer was washed with saturated sodium chloride solution, dried over sodium sulfate/magnesium sulfate, and the ethyl acetate was removed under reduced pressure.

The t-butyldimethylsilyl protecting group was removed by dissolving the residue in 50 mL anhydrous acetonitrile and adding tetraethyl-ammonium fluoride dihydrate (6.21 g, 33.5 mmol). After stirring for 1 hour under nitrogen at room temperature, the reaction was concentrated and the residue was dissolved in 100 mL ethyl acetate. The mixture was extracted with dilute NaHCO₃ solution (3×75 mL) and with water (1×50 mL). The organic layer was diluted with 100 mL diethyl ether and extracted with 10% citric acid solution (5×20 mL) until no more colored material was extracted. The combined aqueous extracts were adjusted to pH 8.5 using 50% aqueous NaOH solution, and extracted with dichloromethane (3×50 mL). The organic solution was dried (Na₂SO₄/MgSO₄) and concentrated under reduced pressure. The residual solid was filtered through silica gel (EtOAc+2% NH₄OH) to give 2.08 g (5.93 mmol) of a mixture of benzhydryl epimers as a light tan solid. Crystallization from ethyl acetate/heptane gave 0.85 g (2.42 mmol) of 3-((S)-((2S,5R)-4-allyl-2,5-dimethyl-1-piperazinyl)(2-methylphenyl)methyl)phenol as white, fluffy needle crystals. ¹H NMR (600 MHz, d₆-DMSO): δ 9.25 (s, 1H), 7.58 (d, J=7.8 Hz, 1H), 7.17 (dt, J=2.0, 7.2 Hz, 1H), 7.04-7.08 (m, 3H), 6.70 (d, J=7.7 Hz, 1H), 6.68 (s, 1H) 6.58 (dd, J=1.8, 8.0 Hz, 1H), 5.73-5.80 (m, 1H), 5.15 (dd, J=1.7, 17.2 Hz, 1H), 5.07 (dd, J=0.9, 10.1 Hz, 1H), 4.90 (s, 1H), 3.10 (dd, J=5.3, 13.9 Hz, 1H), 2.86 (dd, J=6.8, 13.9 Hz, 1H), 2.75-2.78 (m, 1H), 2.69 (dd, J=3.1, 11.1 Hz, 1H), 2.49-2.53 (m, 1H—partially obscured by DMSO peak), 2.19 (s, 3H), 2.06 (dd, J=6.1, 11.1 Hz, 1H), 1.97 (dd, J=5.6, 11.3 Hz, 1H), 0.98 (d, J=6.4 Hz, 3H), 0.92 (d, J=6.4 Hz, 3H). Calculated for C₂₃H₃₀N₂O: C, 78.82; H, 8.63; N, 7.99%. Found: C, 78.89; H, 8.67; N, 8.09%. This material was converted to the hydrochloride salt and lyophilized from H₂O as a fluffy, white solid. Calculated for C₂₃H₃₀N₂O.1.1 HCl.0.35 H₂O: C, 69.60; H, 8.08; N, 7.06; Cl, 9.83%. Found: C, 69.57; H, 8.05; N, 6.93; Cl, 9.77%.

Example 8

4-(alpha-S)-alpha-((2S,5R)-4-(4-Bromobenzyl)-2,5-dimethyl-1-piperazinyl)benzyl)-N,N-diethylbenzamide The title compound was prepared by alkylation of 4-((alpha-S)-alpha-((2S,5R)-2,5-dimethyl-1-piperazinyl)benzyl)-N,N-diethylbenzamide (from Example 1) with 4-bromobenzyl bromide in similar fashion to the process for Example 1. (Yield 89.87%). Calc. for C₃₁H₃₈BrN₃O: C, 67.87; H, 6.98; N, 7.66; Br, 14.57. Found C, 68.00; H, 7.02; N, 7.68; Br, 14.44% ¹H NMR (CDCl₃, 600 MHz); δ 1.06 (d, J=6.2 Hz, 3H); 1.10 (d, J=6.1 Hz, 3H, overlapping br m, 3H); 1.23 (br m, 3H); 1.94 (br t, J=9.4 Hz, 1H); 2.01 (dd, J=11.1, 8.1 Hz, 1H); 2.54 (m, 2H); 2.65 (d, J=9.2 Hz, 2H); 3.13 (d, J=13.4 Hz, 1H); 3.27 (br m, 2H); 3.54 (br m, 2H); 3.83 (d, J=13.5 Hz, 1H); 5.15 (s, 1H); 7.17 (d, J=8.1 Hz, 2H); 7.21 (d, J=7.5 Hz, 2H); 7.27 (d, J=6.2 Hz, 1H, partially obscured by CHCl₃); 7.29 (d, J=8.1 Hz, 2H); 7.32 (br t, J=7.4 Hz, 2H); 7.39 (d, J=8.3 Hz, 2H); 7.46 (d, J=8.1 Hz, 2H).

Example 9

N-(3-Fluorophenyl)-N-methyl-3-((piperidin-4-ylidene)(3-hydroxyphenyl)methyl)-benzamide A mixture of piperidine-4-carboxylic acid ethyl ester (50 g), di-tert-butyl dicarbonate (76.4 g) and Na₂CO₃ (64.4 g) in H₂O/THF (530 mL/212 mL) was refluxed for 2 h. After being cooled to room temperature, the reaction mixture was extracted with EtOAc (400 mL×3). The combined organic layer was washed by water (500 mL×1) and brine (500 mL×1), dried over MgSO₄ and concentrated to give piperidine-1,4-dicarboxylic acid 1-tert-butyl ester 4-ethyl ester (85.6 g). ¹H NMR (600 MHz, DMSO-d₆) δ 4.04 (q, 2H, J=7.0 Hz), 3.81 (m, 2H), 2.80 (bs, 2H), 2.48 (m, 1H), 1.77 (m, 2H), 1.37 (m, 2H), 1.36 (s, 9H), 1.16 (t, J=7.0 Hz).

To a mixture of the above product and NHMe(OMe):HCl (48.6 g) in dry THF (650 mL) was added i-PrMgCl (2.0 M solution in THF, 498.4 mL, 996.8 mmol) at −20° C. The resulting solution was stirred for 2 h at −5° C. and then quenched with aqueous HN₄Cl solution and extracted with EtOAc (800 mL×2). The combined organic layers were washed with brine, dried over MgSO₄ and concentrated to give 4-(N-methoxy-N-methylcarbamoyl)piperidine-1-carboxylic acid tert-butyl ester (80.3 g). ¹H NMR (600 MHz, CDCl₃) δ 4.08 (m, 2H), 3.67 (s, 3H), 3.14 (s, 3H), 2.76 (bs, 3H), 1.63 (m, 4H), 1.41 (s, 9H).

To the solution of (3-bromophenoxy)-tert-butyldimethylsilane (from Example 5, 6.12 g) in THF (120 mL) at −75° C. was slowly added nBuLi (9.37 mL of 2.5 M solution) under nitrogen. After 15 minutes, the solution of 4-(N-methoxy-N-methylcarbamoyl)piperidine-1-carboxylic acid tert-butyl ester (5.80 g) in THF (10 mL) was dropwise added. The reaction was stirred under nitrogen overnight while it warmed to room temperature. The reaction was quenched by slow addition of aqueous NH₄Cl solution (80 mL). The resulting mixture was extracted by EtOAc (120 mL). The organic layer was washed by water (80 mL×3) and brine (80 mL×1), dried by Na2SO4 and concentrated to give crude product (9.13 g), which was purified to afford pure 4-[3-(tert-butyl-dimethyl-silanyloxy)benzoyl]piperidine-1-carboxylic acid tert-butyl ester (5.12 g; 57%). ¹H NMR (600 MHz, DMSO-d₆) δ 7.60 (d, 1H, J=8.0 Hz), 7.41 (dd, 1H, J=8.0, 8.0 Hz), 7.32 (m, 1H), 7.11 (dd, 1H, J=8.0, 2.5 Hz), 3.94 (m, 2H), 3.57 (m, 1H), 2.90 (bs, 2H), 1.72 (m, 2H), 1.38 (s, 9H), 1.37 (m, 2H), 0.94 (s, 9H), 0.19 (s, 6H).

A mixture of 3-iodobenzoic acid (15.0 g) and SOCl₂ (120 mL) was refluxed under nitrogen for 1 h. The solution was cooled to room temperature and concentrated by rotary evaporator to remove SOCl₂. The residual, 3-iodobenzoyl chloride, was dried by vacuum for 2 h and then was dissolved in CHCl₃ (200 mL) and stirred under nitrogen at 0° C. for 20 minutes. To the solution 3-fluorophenylamine (6.72 g) was added dropwise, followed by the addition of Et₃N (12.24 g). After being stirred at room temperature under nitrogen overnight, the reaction was quenched by the addition of water (10 mL). The resulting mixture was washed by water (100 mL×3) and brine (100 mL×1), dried by Na₂SO₄ and concentrated to give crude product (19.8 g), which was recrystallized from CHCl₃ to afford pure N-(3-fluoro-phenyl)-3-iodobenzamide as a white solid (13.5 g; 71%). ¹H NMR (600 MHz, DMSO-d₆) δ 10.47 (s, 1H), 8.27 (s, 1H), 7.94 (m, 2H), 7.71 (m, 1H), 7.53 (m, 1H), 7.40-7.32 (m, 2H), 6.93 (m, 1H).

Sodium hydride (1.11 g of 60% NaH in mineral oil) was added to a solution of CH₃I (4.53 g) and N-(3-fluorophenyl)-3-iodobenzamide (7.26 g) in DMF (120 mL) at 0° C. under nitrogen. After being stirred at 0° C. for another 5 minutes, the reaction was stirred at room temperature under nitrogen for 4 h. The reaction was quenched by slow addition of saturated aqueous NH₄Cl (120 mL), followed by addition of water (100 mL). The mixture was extracted with diethyl ether (300 mL×2). The combined ether layers were washed by water (150 mL×4) and brine (150 mL×1), dried by Na₂SO₄ and concentrated to give crude product (7.56 g), which was purified by column chromatography to afford N-(3-fluoro-phenyl)-3-iodo-N-methylbenzamide (5.88 g; 78%). ¹H NMR (600 MHz, DMSO-d₆) δ 7.64 (m, 2H), 7.28 (m, 1H), 7.24 (d, 1H, J=7.5 Hz), 7.19 (m, 1H), 7.04-6.99 (m, 3.33 (s, 3H).

n-Butyllithium (1.61 mL of 1.92 M solution; 3.10 mmol) was added to a mixture of N-(3-fluorophenyl)-3-iodo-N-methylbenzamide (1.0 g; 2.82 mmol) and 4-[3-(tert-butyl-dimethyl-silanyloxy)benzoyl]-piperidine-1-carboxylic acid tert-butyl ester (1.182 g; 2.82 mmol) in THF (150 mL) at −78° C. under nitrogen in one portion. The reaction was stirred under nitrogen overnight while the temperature warmed to room temperature. Saturated NH₄Cl solution (25 mL) was added to the reaction mixture, followed by the addition of 25 mL of water. The mixture was extracted by ether (300 mL×2). The ether layer was washed by water (200 mL×2) and brine (200 mL×1), dried by Na$_2$SO$_4$ and concentrated to give 2.03 g of crude product, which was purified by silica gel column chromatography eluted with 30% EtOAc in pentane to give 4-([3-(tert-butyldimethylsilanyloxy)phenyl]{3-[N-(3-fluorophenyl)-N-methylcarbamoyl]phenyl}hydroxymethyl)piperidine-1-carboxylic acid tert-butyl ester (763 mg; 42%). $^1$H NMR (600 MHz, DMSO-d$_6$) δ 7.34 (bs, 1H), 7.29 (s, 1H), 7.23-7.16 (m, 3H), 7.09 (m, 2H), 6.94 (m, 2H), 6.85 (m, 2H), 6.60 (d, 1H, J=7.0 Hz), 5.25 (s, 1H), 3.88 (m, 2H), 3.35 (s, 3H), 2.60 (bs, 2H), 2.34 (m, 1H), 1.37 (s, 9H), 1.36 (m, 2H), 1.16 (m, 2H), 0.91 (s, 9H), 0.12 (s, 6H).

A mixture of 4-([3-(tert-butyldimethylsilanyloxy)phenyl]{3-[N-(3-fluorophenyl)-N-methyl-carbamoyl]phenyl}hydroxymethyl)piperidine-1-carboxylic acid tert-butyl ester (3.59 g) and p-toluenesulfonic acid monohydrate (3.5 g) in benzene (200 mL) was refluxed overnight in a round bottom flask equipped with Dean-Stark trap. The reaction solution was cooled to room temperature. Saturated Na$_2$CO$_3$ solution (50 mL) was added to the solution, followed by the addition of 100 mL of H$_2$O. The resulting mixture was extracted by EtOAc (300 mL). It was observed that solids were floating between the two layers. Consequently, 75 ml of 0.5 M NaOH solution was added to the mixture. After being stirred for 30 minutes, the mixture became clear. The organic layer and water layer were separated. The water layer was extracted by EtOAc (100 mL×1). The combined organic layer was washed by water (75 mL×2) and brine (75 mL×1), dried by Na$_2$SO$_4$ and concentrated to give 4-([3-(tert-butyl-dimethylsilanyloxy)phenyl]{3-[N-(3-fluorophenyl)-N-methylcarbamoyl]phenyl}-methylene)piperidine-1-carboxylic acid tert-butyl ester (2.83 g; crude). TLC and $^1$H NMR of the crude product indicated a mixture of compounds, apparently including the desired dehydration product with the loss of N-Boc and/or O-TBDMS protecting groups. The crude product was carried to next step without purification.

Tetrahydrofuran (70 mL) and 3 N HCl (50 mL) were added to the above crude 4-([3-(tert-butyldimethylsilanyloxy)phenyl]{3-[N-(3-fluorophenyl)-N-methylcarbamoyl]phenyl}-methylene)piperidine-1-carboxylic acid tert-butyl ester (2.75 g). The resulting mixture was stirred at 60° C. for 4 h. The reaction mixture was cooled to room temperature, followed by the addition of water (100 mL). The resulting solution was extracted with diethyl ether (100 mL×2). The remaining water layer was neutralized to pH≅9. by 10% NaOH. The water layer became cloudy at this stage. The cloudy water mixture was extracted by n-butanol (100 mL×3). The combined n-butanol layers were washed by water (75 mL×2) and brine (75 mL×1), dried by Na$_2$SO$_4$ and concentrated to give crude product (2.27 g; crude), which was purified to give N-(3-fluorophenyl)-3-[(3-hydroxyphenyl)-piperidin-4-ylidene-methyl]-N-methyl-benzamide (579 mg). $^1$H NMR (600 MHz, DMSO-d$_6$) δ 9.25 (s, 1H), 7.23 (m, 3H), 7.09 (d, 1H, J=10.0 Hz), 7.03 (dd, 1H, J=8.0, 8.0 Hz), 6.96 (ddd, 1H, J=8.5, 8.5, 2.5 Hz), 6.92 (m, 2H), 6.85 (s, 1H), 6.56 (dd, 1H, J=8.0, 2.0 Hz), 6.34 (s, 1H), 6.31 (d, 1H, J=7.5 Hz), 3.35 (s, 3H), 2.65 (m, 2H), 2.55 (m, 2H), 2.13 (bs, 1H), 2.07 (m, 2H), 1.72 (m, 2H); Found: C, 72.87; H, 6.51; N, 5.86. Calc. C, 72.77; H, 6.62; N, 5.98.

Example 10

3-((S)-((2S,5R)-2,5-Dimethyl-1-piperazinyl)(2-methylphenyl)methyl)phenol

The allyl group was removed from 3-((S)-((2S,5R)-4-allyl-2,5-dimethyl-1-piperazinyl)(2-methylphenyl)methyl)phenol (Example 7, 1.07 g, 2.2 mmol) using Pd(dba)2/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 50 mL ethyl acetate and 50 mL diethyl ether. After washing this with Na$_2$CO$_3$ solution (2×50 mL) and water (1×50 mL), the organic solution was extracted with 3 N HCl (4×20 mL). The acidic extract was adjusted to pH 8.5 using 50% aqueous NaOH solution and extracted with dichloromethane (3×25 mL). The solution was dried (Na$_2$SO$_4$/MgSO$_4$) and concentrated under reduced pressure. The residual oil was purified by chromatography on silica gel (EtOAc+2% NH$_4$OH) to give 0.54 g (1.2 mmol) of a viscous, pale amber-colored oil.

The above free amine (0.50 g, 1.1 mmol) was suspended in 20 mL ethanol, 10 mL of 10% w/v aqueous NaOH solution was added, and the reaction was stirred 2 hours at room temperature. The ethanol was removed under vacuum and the residue was partitioned between water and dichloromethane. The solution was adjusted to pH 8.5 using 3 N HCl, separated and extracted again with dichloromethane (2×20 mL). The solution was dried (Na$_2$SO$_4$/MgSO$_4$) and concentrated under reduced pressure. The residual oil gave 0.39 g (1.1 mmol) of the desired product as a light tan foam. $^1$H NMR (600 MHz, d$_6$-DMSO): δ 9.28 (br s, 1H), 7.46 (d, J=7.8 Hz, 1H), 7.16 (br t, J~7.4 Hz, 1H), 7.06-7.11 (m, 3H), 6.59-6.62 (m, 2H), 6.56 (s, 1H), 5.12 (s, 1H), 2.87 (dd, J=2.8, 11.8 Hz, 1H), 2.73-2.78 (m, 1H), 2.56-2.62 (m, 1H), 2.47-2.50 (m, 1H—partially obscured by DMSO peak), 2.44 (dd, J=8.8, 11.8 Hz, 1H), 2.11 (s, 3H), 1.74 (dd, J=8.7, 11.3 Hz, 1H), 0.98 (d, J=6.4 Hz, 3H), 0.87 (d, J=6.4 Hz, 3H). Calculated for C$_{20}$H$_{26}$N$_2$O.0.3 H$_2$O.0.35 CH$_2$Cl$_2$: C, 70.73; H, 7.96; N, 8.11%. Found: C, 70.78; H, 7.87; N, 8.08%. This material was converted to the hydrochloride salt and lyophilized from H$_2$O as a fluffy, beige/tan solid. Calculated for C$_{20}$H$_{26}$N$_2$O.0.95 HCl.0.90 H$_2$O: C, 66.49; H, 8.02; N, 7.75; Cl, 9.32%. Found: C, 66.36; H, 7.86; N, 7.61; Cl, 9.23%.

Example 11

4-(4-[(R)-(4-Dimethylsulfamoylphenyl)-(3-hydroxyphenyl)methyl]-(2S,5R)-dimethyl-piperazin-1-ylmethyl)benzoic acid t-Butyldimethylchlorosilane (26.01 g; 172.56 mmol) was added to a solution of 3-hydroxybenzaldehyde (20.7 g; 164.35 mmol) and imidazole (27.97 g; 410.9 mmol) in CHCl$_3$ (300 mL) at 0° C. via a funnel. The reaction was stirred under N$_2$ overnight while it warmed to room temperature. The reaction mixture was washed by water (100 mL×3) and brine (100 mL×1), dried over Na$_2$SO4 and concentrated to give crude product (29.56 g), which was purified by column chromatography eluted by (i) pentane and (ii) 3% EtOAc in pentane to give 3-(t-butyl-dimethyl-silanyloxy)-benzaldehyde (21 g; 54%). $^1$H NMR (300 MHz, CDCl$_3$) δ 9.93 (s, 1H), 7.45 (d, 1H, J=7.5 Hz), 7.38 (dd, 1H, J=7.5, 7.5 Hz), 7.31 (d, 1H, J=1.0 Hz), 7.09 (1H, dd, J=7.5, 1.0 Hz), 0.98 (s, 9H), 0.20 (s, 6H).

Dimethylamine (100 mL of 2.0 M THF solution; 200 mmol) was added to a solution of pipsyl chloride (54.76 g; 181 mmol) in pyridine (300 mL) at 0° C. under N$_2$, followed by the addition of N,N-dimethylaminopyridine (15 mg). The reaction was stirred under N$_2$ for two days while it warmed from 0° C. to room temperature. The reaction solution was poured into 1.2 liter of water. The desired product was precipitated out of the H$_2$O/pyridine solution. The solid was collected by filtration and rinsed by H$_2$O (300 mL×2). The solid was dissolved in EtOAc (500 mL). The EtOAc solution was washed by 5% aqueous HCl (300 mL×3), water (300 mL×2) and brine (300 mL×1), dried by Na$_2$SO$_4$ and concentrated to give 4-iodo-N,N-dimethylbenzenesulfonamide (49.46 g; 88%) as white solid, which was used in the next reaction without further purification. $^1$H NMR (300 MHz, CDCl$_3$) δ 7.88 (d, 2H, J=8.5 Hz), 7.46 (d, 2H, J=8.5 Hz), 2.69 (s, 3H).

4-{(R)-((2R,5S)-4-Allyl-2,5-dimethyl-piperazin-1-yl)-[3-(tert-butyl-dimethylsilanyloxy)-phenyl]-methyl}-N,N-dimethyl-benzenesulfonamide Part 1—Preparation of Iminium Intermediate:
To a 3-neck flask equipped with a Soxhlet extractor filled with molecular sieves was added benzotriazole (618 mg; 5.19 mmol), 3-(t-Butyl-dimethyl-silanyloxy)-benzaldehyde (1.227 g; 5.19 mmol), (+)-(2S,5R)-1-allyl-2,5-dimethylpiperazine (961 mg; 6.23 mmol) and toluene (150 mL). The solution was refluxed under N$_2$ for 20 h and cooled to room temperature.
Part 2—Preparation of Grignard Reagent:
Isopropylmagnesium chloride (6.91 mL of 2.0 M THF solution; 13.82 mmol) was added to a solution of 4-iodo-N,N-dimethyl-benzenesulfonamide (4.3 g; 13.82 mmol) at room temperature under N$_2$. After being stirred for 20 minutes, TLC of the reaction mixture indicated the formation of a new spot and the disappearance of the starting material.
Part 3—Reaction of Intermediates:
The solution of Part 1 was added to the Grignard reagent prepared in Part 2 dropwise via a syringe at room temperature under N$_2$ in a span of 35 minutes while the reaction solution was stirred vigorously. The reaction was stirred at room temperature under N$_2$ overnight. The reaction was quenched by the addition of saturated aqueous NH$_4$Cl (10 mL). The resulting mixture was diluted by the addition of EtOAc (120 mL) and water (120 mL). The cloudy mixture was filtered through a Celite pad. The filtrate was poured into a separatory funnel. The organic layer and water layer were separated. The organic layer was extracted by 10% aqueous NaOH (75 mL×4), washed by water (100 mL×3) and brine (100 mL×1), dried (Na$_2$SO$_4$) and concentrated to give crude product, which was purified by silica gel chromatography conducted on CombiFlash™ Sq 16x (gradient: 100% CH$_2$Cl$_2$ to 7% MeOH in CH$_2$Cl$_2$) to give 4-{(R)-((2R,5S)-4-allyl-2,5-dimethyl-piperazin-1-yl)-[3-(tert-butyl-dimethylsilanyloxy)-phenyl]-methyl}-N,N-dimethyl-benzenesulfonamide (1.3 g; 45%). $^1$H NMR (300 MHz, CDCl$_3$) δ 7.71 (d, 2H, J=8.0 Hz), 7.35 (d, 2H, J=8.0 Hz), 7.12 (dd, 1H, J=8.0, 8.0 Hz), 6.92 (s, 1H), 6.84 (d, 1H, J=8.0 Hz), 6.71 (d, 1H, J=8.0 Hz), 5.82 (1H, m), 5.23-5.11 (m, 3H), 3.35 (dd, 1H, J=14.0, 5.5 Hz), 2.88 (dd, 1H, J=14.0, 8.0 Hz), 2.82 (dd, 1H, J=11.0, 3.0 Hz), 2.73 (s, 6H), 2.68 (dd, 1H, J=11.0, 2.5 Hz), 2.55 (m, 2H), 2.16 (dd, 1H, J=11.0, 8.5 Hz), 1.85 (dd, 1H, J=11.0, 9.0 Hz), 1.18 (d, 3H, J=6.0 Hz), 1.01 (d, 3H, J=6.0 Hz), 0.96 (s, 9H), 0.17 (s, 3H), 0.16 (s, 3H).

4-[(R)-((2R,5S)-4-Allyl-2,5-Dimethylpiperazin-1-yl)-(3-hydroxy-phenyl)methyl]-N,N-dimethylbenzenesulfonamide Aqueous hydrochloric acid (3 M, 7 mL) was added to a solution of 4-{(R)-((2R,5S)-4-allyl-2,5-dimethyl-piperazin-1-yl)-[3-(tert-butyl-dimethylsilanyloxy)-phenyl]-methyl}-N,N-dimethyl-benzenesulfonamide (1.3 g) in THF (15 mL). The mixture was stirred at room temperature overnight. Water (15 mL) was added to the reaction. The reaction mixture was extracted with diethyl ether (25 mL×3). The remaining H$_2$O layer was neutralized by 10% aqueous NaOH to pH=8-9 and then extracted by EtOAc (30 mL×3). The combined EtOAc layers were washed by water (20 mL×3) and brine (20 mL×1), dried over Na$_2$SO$_4$ and concentrated to give 0.83 g of crude product. The crude product was purified by silica gel chromatography conducted on CombiFlash™ Sq 16x (gradient: 100% CH$_2$Cl$_2$ to 7% MeOH in CH$_2$Cl$_2$) to give 4-[(R)-((2R,5S)-4-allyl-2,5-dimethylpiperazin-1-yl)-(3-hydroxy-phenyl)methyl]-N,N-dimethylbenzenesulfonamide (720 mg; 70%).
$^1$H NMR (300 MHz, CDCl$_3$) δ 7.71 (d, 2H, J=8.5 Hz), 7.35 (d, 2H, J=8.5 Hz), 7.14 (dd, 1H, J=8.0, 8.0 Hz), 6.89 (bs, 1H), 6.85 (d, 1H, J=8.0 Hz), 6.68 (d, 1H, J=8.0, 2.5 Hz), 5.83 (1H, m), 5.24-5.12 (m, 3H), 3.32 (dd, 1H, J=13.5, 5.0 Hz), 2.86 (dd, 1H, J=13.5, 8.0 Hz), 2.78 (dd, 1H, J=11.5, 3.0 Hz), 2.72 (s, 6H), 2.65 (dd, 1H, J=11.0, 2.5 Hz), 2.51 (m, 2H), 2.14 (dd, 1H, J=11.5, 9.0 Hz), 1.81 (dd, 1H, J=11.0, 9.5 Hz), 1.16 (d, 3H, J=6.0 Hz), 0.98 (d, 3H, J=6.0 Hz); MS (FAB, glycerol) m/z: 444 (M$^+$+H), 290, 153; Found: C, 58.32; H, 6.66; N, 8.18. Calc. (C$_{24}$H$_{33}$N$_3$O$_3$S 0.8 CH$_2$Cl$_2$): C, 58.23; H, 6.82; N, 8.21.

Bis(dibenzylideneacetone)palladium (199 mg) was added to a solution of 1,4-bis(diphenylphosphino)butane (148 mg) in THF (4 mL) under nitrogen at room temperature for 10 minutes. The resulting Pd-catalyst [J. P. Genet, S. Lemaire-Audoire, M. Savignac, Tetrahedron Letters, 36, 1267-1270 (1995)] was transferred to a solution of 4-[(R)-((2R,5S)-4-allyl-2,5-dimethyl-piperazin-1-yl)-(3-hydroxy-phenyl)-methyl]-N,N-dimethyl-benzenesulfonamide (3.08 g) and thiosalicylic acid (1.28 g) in THF (130 mL) via a syringe. The reaction was stirred under nitrogen at room temperature overnight. The reaction mixture was concentrated and EtOAc (350 mL) was added to the remaining residue, followed by the addition of 1N aqueous HCl (300 mL). The resulting mixture was poured into a separatory funnel. The EtOAc layer and acidic water layer were separated. The acidic water layer was extracted by EtOAc (100 mL×3). The acidic water layer was neutralized by 1N NaOH solution to pH≅8. Solid precipitate in the water solution was observed at this stage. The cloudy water mixture was extracted by EtOAc:MeOH=95:5 (200 mL×4). The combined organic layer was washed by water (100 mL×1), dried by Na$_2$SO$_4$ and concentrated to give 2.46 g of crude product, which was purified to afford 4-[(R)-(3-hydroxyphenyl)-((2R,5S)-dimethylpiperazin-1-yl)-methyl]-N,N-dimethyl-benzenesulfonamide (1.82 g, 65%). $^1$H NMR (300 MHz, DMSO-d$_6$) δ 9.28 (s, IH), 7.74 (d, 2H, J=8.0 Hz), 7.43 (d, 2H, J=8.0 Hz), 7.09 (dd, 1H, J=8.0, 8.0 Hz), 6.78 (s, 1H), 6.69 (d, 1H, J=8.0 Hz), 6.61 (d, 1H, J=8.0 Hz), 5.33 (s, 1H), 2.81-2.72 (m, 2H), 2.62 (s, 6H), 2.62-2.40 (m, 2H), 2.13 (m, 1H), 1.87 (bs, 1H), 1.39 (1H, dd, J=10.0, 10.0 Hz).

A mixture of 4-[(R)-(3-hydroxyphenyl)-((2R,5S)-dimethylpiperazin-1-yl)methyl]-N,N-dimethylbenzenesulfonamide (210 mg), 4-carboxybenzaldehyde (156 mg) and acetic acid (63 mg) in 10 mL of THF and 5 mL of DMF was stirred under nitrogen at room temperature for 30 minutes. Sodium triacetoxyborohydride (276 mg) was added to the solution. The reaction was stirred under nitrogen at room temperature overnight. The reaction was quenched by the addition of water (2 mL). The resulting mixture was concentrated under vacuum to remove THF. The remaining residue was diluted by H$_2$O (70 mL) to give a cloudy water mixture with pH≅5. The water layer was neutralized by 1 M NaOH solution to pH≅8. White solid (desired product) was floating in the water mixture. The mixture was filtered and the solid was rinsed by water (15 mL×2). The solid was dissolved in EtOAc (60 mL). The EtOAc solution was washed by water (40 mL×1) and brine (40 mL×1), dried by Na$_2$SO$_4$ and concentrated to give crude product, which was purified by silica gel chromatography conducted on CombiFlash™ Sq 16x (gradient: 100% CH$_2$Cl$_2$ to 10% MeOH in CH$_2$Cl$_2$) to give 4-{4-[(R)-(4-dimethylsulfamoyl-phenyl)-(3-hydroxyphenyl)methyl]-(2S,5R)-dimethylpiperazin-1-ylmethyl}benzoic acid as a white solid (148 mg; 53%). $^1$H NMR (300 MHz, CD$_3$OD) δ 7.97 (d, 2H, J=8.0 Hz), 7.77 (d, 2H, J=8.5 Hz), 7.57 (d, 2H, J=8.5 Hz), 7.45 (d, 2H, J=8.0 Hz), 7.12 (dd, 1H, J=8.0 Hz), 6.89 (s, 1H), 6.84 (d, 1H, J=8.0), 6.66 (dd, 1H, J=8.0, 2.0 Hz), 5.22 (s, 1H), 4.16 (d, 1H, J=13.5 Hz), 3.67 (d, 1H, J=13.5 Hz), 2.99-2.87 (m, 3H), 2.68 (s, 6H), 2.64 (m, 1H), 2.38 (m, 1H), 2.11 (m, 1H), 1.93 (d, 3H, J=6.5 Hz), 1.15 (d, 3H, J=6.5 Hz). MS (FAB, glycerol) m/z: 538.1 ($M^+$+H), 404.2, 290.2; Found: C, 63.28; H, 6.69; N, 7.39. Calc. ($C_{29}H_{35}N_3O_5S$ 0.9 $CH_3OH$): C, 58.23; H, 6.82; N, 8.21.

Example 12

N,N-Diethyl-3-((R)-((2S,5R)-2,5-dimethyl-4-(pyridin-4-yl-methyl)piperazin-1-yl)(3-hydroxyphenyl)methyl)benzamide 3-Carboxybenzaldehyde (150 g, 100 mmol) was weighed in a 250 mL, 3-necked, round bottom flask and stirred under nitrogen in 110 mL of toluene. Thionyl chloride (8.75 mL, 120 mmol) was added to the mixture, followed by the addition of 6 drops of DMF. A reflux condenser fitted with a calcium chloride drying tube was placed on the flask. The reaction was placed in an oil bath and heated at a bath temperature maintained below 120° C. The mixture was allowed to reflux for 1 hour after a clear solution was obtained and then cooled to room temperature. The solution was diluted with anhydrous toluene, and all volatiles were removed under vacuum.

The crude acid chloride was dissolved in 200 mL of dry tetrahydrofuran and cooled in an ice/water bath. Triethylamine (27.88 mL, 200 mmol) in 70 mL of dry tetrahydrofuran was added dropwise via an addition funnel, followed by diethylamine (10.45 mL, 100 mmol). The cloudy solution was allowed to warm to room temperature over 1 hour and stirred overnight. Water was added and the product was extracted with dichloromethane. The organic layer was washed with water and saturated sodium chloride solution and dried over sodium sulfate, and the solvent was removed under vacuum. 3-Formyl-N,N-diethylbenzamide (17.72 g) was obtained as a light golden oil (86% unchromatographed yield). $^1$H NMR (300 MHz, DMSO-$d_6$): δ 1.04-1.18 (m, 6H); 3.17-3.45 (m, 4H); 7.65-7.66 (m, 2H); 7.85 (s, 1H); 7.93-7.94 (m, 1H); 10.03 (s, 1H).

2R,5S-1-allyl-2,5-dimethylpiperazine (2.31 g, 15 mmol, Chirotech Division of Dow Pharma, Cambridge, England), benzotriazole (1.80 g, 15.15 mmol, 1.01 eq.), and 3-formyl-N,N-diethylbenzamide (3.08 g, 15 mmol) were mixed in 150 mL of dry toluene with two drops of triethylamine. The mixture was placed in an oil bath maintained below 140° C. (bath temperature). The flask was attached to a Dean-Stark trap and reflux condenser to allow the azeotropic removal of water. The mixture was refluxed for 2-3 hours, under a nitrogen atmosphere, then the majority of the toluene was removed under reduced pressure. The crude adduct was used in the following procedure without isolation.

The crude benzotriazole adduct was dissolved in ~20 mL of tetrahydrofuran and added to a solution of 3-phenoxy-tert-butyldimethylsilane magnesium bromide (from Example 5, 1.75 equiv.) via a double-ended needle. After stirring under nitrogen at room temperature for 2 hours, the reaction was quenched with 6-8 mL of saturated ammonium chloride solution. After stirring for 30 minutes, a generous amount of anhydrous magnesium sulfate was added. Filtering and concentrating the solution under reduced pressure gave the crude silyl ether contaminated with benzotriazole by-product. This residue was dissolved in ethyl acetate and extracted with 10% aqueous NaOH solution three times to remove most of the benzotriazole. The organic layer was washed with saturated sodium chloride solution, dried over sodium sulfate/magnesium sulfate, and the ethyl acetate was removed under reduced pressure.

The t-butyldimethylsilyl protecting group was removed by dissolving the residue in 80 mL of tetrahydrofuran and adding 80 mL of 3N aqueous HCl at room temperature. The solution warmed upon acid addition. The mixture was stirred for 90 minutes at room temperature. The reaction was concentrated under reduced pressure to remove most of the organic solvent. The residue was partitioned between water and a solution of diethyl ether:ethyl acetate/3:2. The acidic aqueous layer was extracted twice with a solution of diethyl ether:ethyl acetate/3:2. The aqueous layer was adjusted to pH=2 using aqueous NaOH solution, at which point cloudiness persisted and a dark oil began to precipitate. Methylene chloride (~100 mL) was added and stirred briskly. This was separated and the aqueous layer was again washed with more methylene chloride. The combined organic extract was partitioned with water, and while stirring vigorously was adjusted to pH=9 using aqueous NaOH solution. This was then separated and the aqueous layer was again washed with more methylene chloride. The combined methylene chloride extract was dried over sodium sulfate/magnesium sulfate, and the solvent was evaporated under reduced pressure. The crude material was chromatographed on a silica gel column (roughly 20-25 g of silica gel per gram of crude material) eluting first with methylene chloride, then with 20% ethyl acetate in methylene chloride to remove the less polar contaminant. Then, the column was eluted with a solution of ethyl acetate containing 2% ammonium hydroxide (solution A) in a gradient with methylene chloride (solution B), quickly increasing in polarity from 25% to 100% (solution A in B). The desired fractions were combined and the solvent was removed under reduced pressure. A 10:1 mixture of diastereomers (approx. 2.01 g) was obtained. Pure product was obtained by crystallization from a hot solution of ethyl acetate (5-10 mL) followed by slow addition of heptane (10-20 mL) and gradual cooling to give 1.35 g of (+)-3-((alphaR)-alpha-((2S,5R)-4-allyl-2,5-dimethyl-1-piperazinyl)-3-hydroxybenzyl)-N,N-diethylbenzamide as an off-white crystalline solid with >98% isomeric purity (as determined by NMR). $^1$H NMR (300 MHz, DMSO-$d_6$): δ 0.90-0.92 (d, J=6.1 Hz, 3H); 0.94-1.04 (m, 6H); 1.06-1.08 (d, J=6.1 Hz, 3H); 1.73-1.76 (m, 2H); 2.01-2.15 (m, 1H); 2.52-2.56 (q, J=11.1 Hz, 2H); 2.69-2.72 (q, J=14.0 Hz, 2H); 2.75-2.82 (q, J=13.9 Hz, 1H) 3.11-3.40 (d, J=4.9 Hz, 2H); 3.56-3.62 (d, J=13.3 Hz, 2H); 5.05-5.11 (dd, $J_1$=6.1 Hz, $J_2$=16.6 Hz, 2H); 5.16 (s, 1H); 5.70-5.82 (m, 1H); 7.13-7.16 (d, J=7.3 Hz, 1H); 7.24-7.41 (m, 7H); 9.31 (s, 1H).

3-((R)-((2S,5R)-4-Allyl-2,5-dimethyl-1-piperazinyl)-3-hydroxybenzyl)-N-diethylbenzamide (4.35 g, 10 mmol), N-phenyltrifluoromethane-sulfonimide (3.82 g, 10.7 mmol), and triethylamine (3.1 mL, 22 mmol) were dissolved in 75 mL dichloromethane and stirred overnight at room temperature under nitrogen. After concentrating under reduced pressure, the residue was dissolved in 100 mL ethyl acetate and washed with $Na_2CO_3$ solution (3×100 mL), water (1×100 mL), and brine (1×100 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 6.01 g (10.59 mmol) of the resulting triflate ester as a viscous, golden yellow oil.

The allyl group was removed using $Pd(dba)_2$/DPPB in the presence of thiosalicylic acid by the method of Genet [J. P. Genet, S. Lemaire-Audoire, M. Savignac, Tetrahedron Letters, 36, 1267-1270 (1995)]. The reaction was concentrated and the residue was dissolved in 50 mL ethyl acetate and 100 mL diethyl ether. After washing this with $Na_2CO_3$ solution (3×100 mL) and water (1×100 mL), the organic solution was extracted with 3 N HCl (3×20 mL) and 1 N HCl (1×20 mL). The acidic extract was adjusted to pH 8.5 using NaOH solution and extracted with dichloromethane (3×25 mL). The solution was dried ($Na_2SO_4/MgSO_4$) and concentrated under reduced pressure. The residual oil was purified by chromatography on silica gel (2% $NH_4OH$ in $EtOAc/CH_2Cl_2$) to give 4.39 g (8.32 mmol) of a viscous, deep amber-orange colored oil.

A solution of above free amine (0.87 g, 1.50 mmol) in acetonitrile (10 mL) was added to sodium iodide (100 mg), sodium carbonate (0.88 g, 8.30 mmol) and stirred under nitrogen at room temperature during the addition of 4-picolyl chloride hydrochloride (0.27 g, 1.65 mmol). The reaction was complete in 6 hours. The solvent was removed by evaporation, the residue was partitioned between methylene chloride and water, and the aqueous layer was extracted with methylene chloride twice more. The combined organic extracts were dried ($Na_2SO_4/MgSO_4$) and concentrated under reduced pressure. The residual dark red amorphous solid was purified by chromatography on silica gel ($EtOAc/CH_2Cl_2=1/1$, then 75% EtOAc with 2% $NH_4OH$ in $CH_2Cl_2$) to give 0.35 g (0.72 mmol) of N,N-diethyl-3-((R)-((2S,5R)-2,5-dimethyl-4-(pyridin-4-yl-methyl)piperazin-1-yl)(3-hydroxyphenyl)-methyl)benzamide as a white amorphous solid. The salt was made by dissolving the base in ethanol and titrating with 0.2M HCl in ethanol to pH 3.60. The resulting salt solution was lyophilized overnight to obtain a white powdery solid. $^1$H NMR (300 MHz, $d_6$-DMSO): δ 0.90-1.10 (m, 12H); 1.90-2.08 (m, 2H); 2.58-2.68 (m, 5H); 3.08-3.50 (m, 4H); 3.68-3.79 (d, J=15.1 Hz, 1H); 4.94 (s, 1H); 6.61-6.76 (m, 3H); 7.07-7.44 (m, 7H); 8.43-8.45 (d, J=5.7 Hz, 2H); 9.32 (s, 1H).: 487.6 (M+1, 100%), 509.3 (30%). Calculated for $C_{30}H_{38}N_4O_2 \cdot HCl\, H_2O$: C, 66.59; H, 7.64; N, 10.35; Cl, 6.55. Found: C, 66.23; H, 7.56; N, 10.23; Cl, 6.73.

Example 13

In vitro Testing of Opioid Receptor Affinity

A group of opioid receptor agonists useful to treat urinary dysfunctions were evaluated for in vitro opioid receptor affinity in rat brain membranes (μ and δ opioid) and guinea pig cerebellum (κ opioid receptor). Membranes for radioligand binding were prepared from either rat whole brain or guinea pig cerebellum, supplied by Pel-Freeze Biological Inc. (Rogers, A R.). Tissues were homogenized in 50 mM TRIS (Tris [hydroxymethyl]aminomethane) buffer (pH 7.4) containing 50 μg/ml soybean trypsin inhibitor, 1 mM EDTA (Ethylenediaminetetraacetic acid), and 100 μM PMSF (Phenylmethylsulfonyl fluoride). The homogenized brain tissues were centrifuged at 500×g for 30 minutes (4° C.) to remove large debris. The supernatant was polytronically sonicated for 10 seconds (P.E. setting of 2, 4° C.). Sucrose solution was then added to a final concentration of 0.35 M using a 10 mM TRIS-Sucrose buffer (pH 7.4) and the brain membranes were then centrifuged at 40,000×g for 30 minutes (4° C.). The membrane pellets were then washed twice in 10 mM TRIS buffer (pH 7.4) containing 50 μg/ml soybean trypsin inhibitor, 1 mM EDTA, and 100 μM PMSF.

Radioligand binding assays were performed in 10 mM TRIS buffer (pH 7.4) containing 50 μg/ml soybean trypsin inhibitor, 1 mM EDTA, 5 mM $MgCl_2$, and 100 μM PMSF. Tritium-labeled DAMGO (μ), Deltorphin II (δ), or U69593 (κ) purchased from New England Nuclear were used as ligands in competitive experiments ($2-3 \times 10^{-10}$ M concentrations) with non-specific binding defined by $0.5 \times 10^{-6}$ M Naloxone (purchased from SIGMA Chemical Co.). All binding assays were run at room temperature for 90 minutes and then terminated by rapid filtration on GF/C glass fiber filters (Whatman, Hillsboro, Oreg.) with 50 mM TRIS buffer (4° C.), pH 7.4) employing a Brandel Semi-automatic Cell Harvester (Model M48, Brandel, Gaithersburg, Md.). The filters were washed twice with 50 mM TRIS buffer (4° C., pH 7.4) and the filters were placed in liquid scintillation cocktail and the bound radioactivity counted on a Beckman LS 6500 scintillation counter. The potency of the compounds in inhibiting the binding of DAMGO (μ), Deltorphin II (δ), or U69593 (κ) was determined as the concentration that reduced the binding of the labeled compounds by 50 percent ($IC_{50}$).

The results of the in vitro testing are compiled in FIG. 1 (Table 1), showing that all the testing compounds had some delta opioid receptor activity, albeit some having greater activity than others.

Example 14

Effect of Delta Opioid Receptor Agonists on Cystometric Parameters in Healthy Conscious Rats Male rats weighing 200 to 250 grams were used. The rats were housed with free access to food and maintained on forced 12 hours alternating light-dark cycle at 22-24° C. for at least one week, except during performance of the experiment.

The rats were anesthetized with pentobarbital, 65 mg/kg i.p. and placed in a supine position. An approximately 10 mm long midline incision was made in the shaved and cleaned abdominal wall. The urinary bladder was freed from adhering tissues, emptied and then cannulated, via an incision at the dome with a polyethylene cannula (PE50), which was permanently sutured in place. The cannula was exteriorized through a subcutaneous tunnel in the retroscapular area, where it was connected with a plastic adapter to avoid the risk of removal by the rats. For intravenous (i.v.) injection of test compounds, a polyethylene tubing (PE50) was inserted into the jugular vein and exteriorized in the retroscapular area. Since cystometrographic parameters have been reported to be influenced by the time elapsed after catheter implantation, the rats were treated with 1 mg/kg Penicilline G, intramuscularly, to prevent infection and allowed to rest 3 days after implantation and before testing commenced.

For oral administration of test compounds, a polyethylene tube (PE50) was inserted into the stomach and was permanently sutured in place. The cannula was exteriorized through a subcutaneous tunnel in the retroscapular area, where it was connected with a plastic adapter to avoid the risk of removal by the rats.

On the day of the experiments, the rats were placed in Bollman's cages, the free tip of the bladder catheter was connected through a T-shaped tube to a pressure transducer (Grass PT300 or Gould P23) to record bladder pressure and to a peristaltic pump for continuous infusion, at a constant rate of 0.1 m/min of saline solution into the urinary bladder. The intraluminal pressure signal during infusion was continuously recorded. Two urodynamic parameters were evaluated: micturition pressure and interval between micturition that equates to volume capacity before detrusor contraction occurs (decrease in frequency of contractions). Micturition pressure is defined as the maximal intravesical pressure induced by the contraction of detrusor during micturition. Data was calculated as the mean of testing results for several animals at each dosage. The drug effects were expressed as a percent relative to activity of the control data, which was set at 100%.

Infusion was commenced with saline solution to determine activity in rats without test compounds to be used as the control baseline. Saline solution infusion was interrupted and the test compounds were administered. At time points 90 minutes after intravenous administration and 120 minutes after oral drug administration, cystometrograms were recorded in each animal and the mean values of the recorded cystometrographic parameters were calculated.

Results of the csytometrographic recordings performed 90 minutes after intravenous injection with several different testing compounds of the present invention are summarized in FIG. 2 (Table 2). In particular, the results indicate that intravenous (i.v.) administration of compounds 1, 2, 3, 4, 10 and 12 effected an inhibition of bladder contractions. Compounds 1-10 and 12 caused a decrease in the frequency of the bladder contractions (increase in the interval between bladder contractions, which reflects an increase in capacity of the bladder). Compounds 1, 2, 3, 4, 10 and 12 affected both parameters by causing a decrease in the intensity of bladder contractions and a decrease in the frequency of the bladder contractions.

Figure 3:
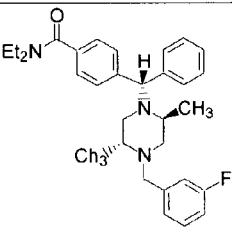
FIG. 3 summarizes the results of cystometric evaluation of two urodynamic parameters for illustrative delta opioid receptor agonists of the present invention that were orally administered.
Figure 3:
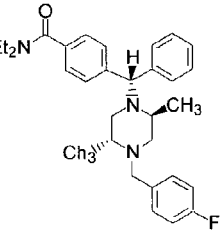
Figure 3:
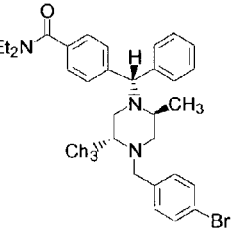
Figure 3:
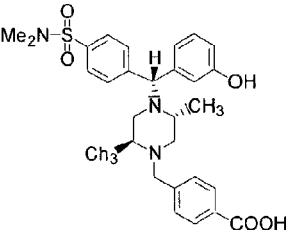

Compounds 1, 2, 8 and 11 were also tested for effectiveness by oral administration via the stomach cannula. The same cystometrographic parameters were tested as above and the results are summarized in Table 3 as set forth in FIG. 3. Oral administration of compounds 1 and 11 produced a decrease in the frequency of bladder contractions and a decrease in the pressure of these contractions, thereby providing for increased capacity of the bladder. Unexpectedly, compound 1 showed similar effectiveness for both methods of administration indicating that similar blood levels of the compound can be achieved with different modes of administration. Interestingly, compound 1 does not comprise a phenolic ring substituted with a hydroxyl group or methylation of the hydroxyl group. It has been speculated that the hydroxyl or methoxy group on the phenol ring is a key pharmacophore for peptide and non-peptide ligands to recognize delta-opioid receptors and produce physiological effects. However, compound 1 has been found to be surprising effective without such a phenolic ring, thereby providing unexpected physiological effects.

Example 15

Effect of Delta Opioid Receptor Agonists on Cystometric Parameters in Rats Experiencing Partial Urethral Restriction Male rats weighing 200 to 250 grams were used. The method to produce bladder outlet obstructions thereby producing partial urethral restriction is essentially that reported by Malmgren et al, *J. Urol*. 137:1291-1294, the disclosure of which is hereby incorporated herein by reference. Following anesthetic induction, the ventral abdominal wall and perineum were shaved and cleaned with betadine. A lower midline abdominal incision was made, and the bladder and proximal urethra were identified. A plastic rod with a ~1 mm outer diameter was placed parallel to the urethra, and a silk ligature was tied around the urethra and the plastic rod. After the ligature was secured, the externally dwelling plastic rod was removed, thus ensuring the lumen diameter was constrained to ~1 mm. Animals were given analgesic buprenorphine and allowed to recover. A second surgical procedure was performed to remove the urethral ligature 6 weeks after its placement and at the time the cystometric catheter is placed. The implantation of the plastic rod for six weeks in the urethra caused inflammation in the area and caused the test rats to experience instability of the bladder muscle similar to those side effects indicative of genuine urinary tract dysfunctions.

On the day of testing, the bladder catheter was connected through a T-shaped tube to a pressure transducer (Grass PT300 or Gould P23) to record bladder pressure isovolumetrically and to a peristaltic pump for continuous infusion, at a constant rate of 0.1 ml/min, of saline solution into the urinary bladder. The pressure signal during infusion was continuously recorded.

Two urodynamic parameters were evaluated in the test rats: micturition pressure and interval between voiding that equates to volume capacity before detrusor contraction occurs (decrease in frequency of contractions). Changes in bladder activity were recorded and expressed as pressure or volume over time.

Figure 4:
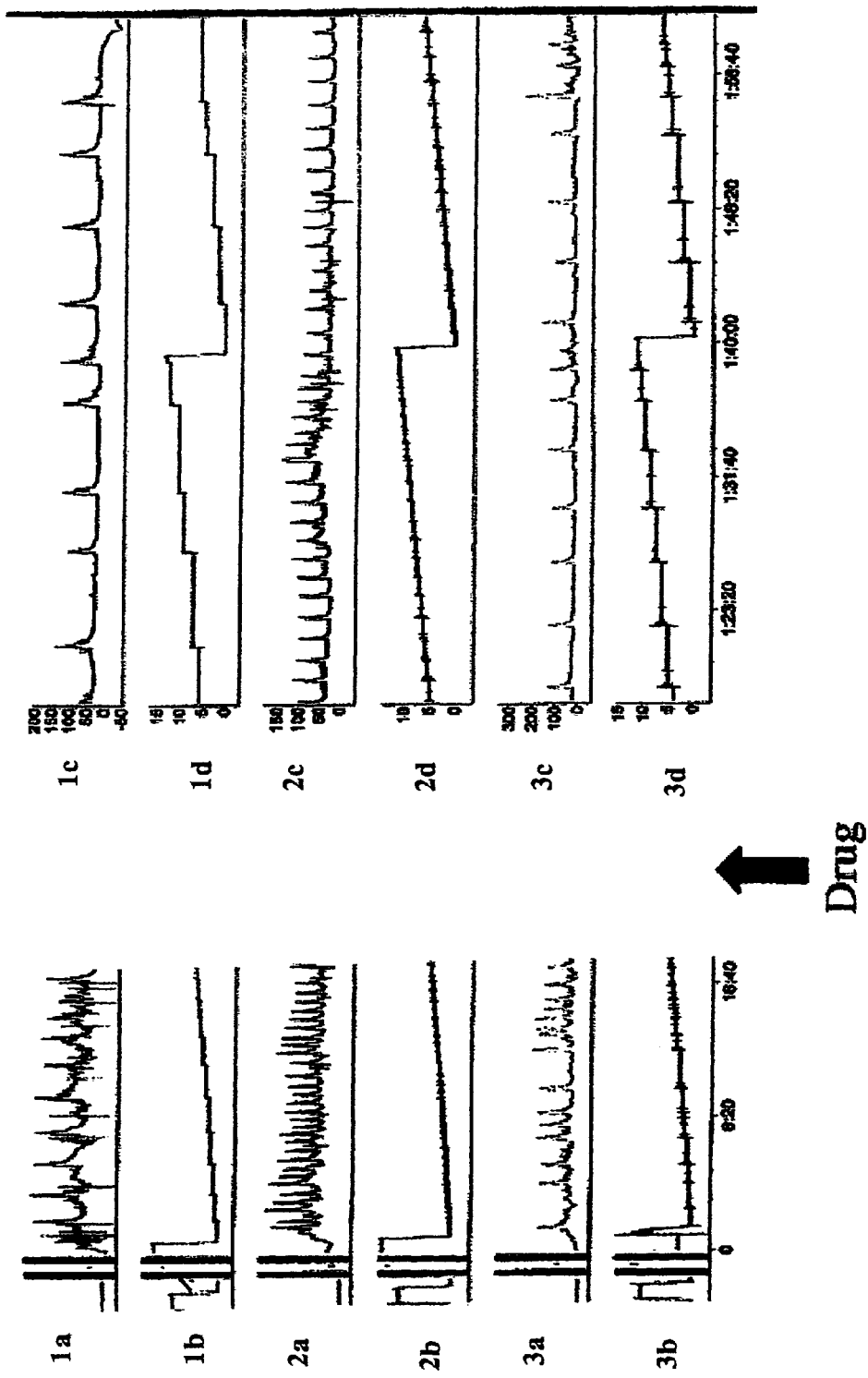
FIG. 4 illustrates cystometric traces of test animals experiencing partial urethral restriction and the effects of orally administering compound 1 in accordance with the present invention. Traces 1a, 1c; 2a, 2c; and 3a, 3c show the micturition pressure change due to bladder contraction and frequency of voiding. Traces 1b, 1d; 2b, 2d; and 3b, 3d show voiding volume collected in the cage.

FIG. 4 shows cystometric traces of urodynamic parameters for three test rats having compromised urinary tracts due to previously implanted obstructions. The traces illustrate urodynamic parameters for the test animals before administration of the testing compound and after oral administration of 10 mg/kg of Compound 1. The traces on the left side of the plot show the pressure and voiding history (1*a* and *b*, 2*a* and *b*, and 3*a* and *b*) of the three test animals before administration of compound 1. Viewing traces 1*a* and 1*b*, it is evident that test animal #1 experienced multiple and strong contraction of the bladder muscle. Further from trace 1*b* it can be recognized that the animal was voiding continuously showing almost no storage of urine in the bladder. The traces for the other two test animals are also indicative of an unstable bladder. After the three test animals were administered the oral dose of compound 1, there was a marked improvement in contractions and volume storage. Traces 1*c* and 1*d* show that the frequency of the contraction and pressure of each contraction was greatly reduced. Further, trace 1*d* shows that the volume capacity increased and the test animal had increased bladder capacity before voiding. Instead of the continuous voiding shown in trace 1*b*, the test animal was voiding intermittently and therefore storing greater volumes of urine between voidings. Clearly, all three-test animals showed marked improvement in both frequency and intensity of pressure contractions (reduced) and quantity of volume storage after administering of compound 1.

What is claimed is:

1. A method for combating a urinary tract dysfunction in a subject in need thereof comprising administering to the subject an effective amount of a delta opioid receptor agonist to combat the urinary tract dysfunction, wherein the delta opioid receptor agonist has the formula:

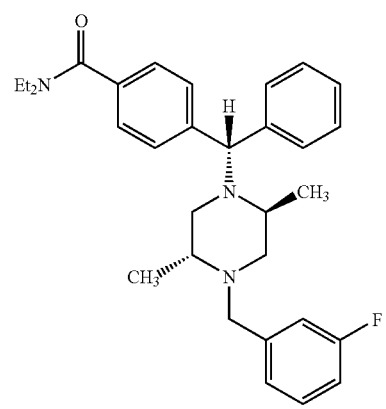

or a pharmaceutically acceptable salt or ester thereof, wherein the urinary tract dysfunction is urinary incontinence.

2. The method according to claim 1, wherein the delta opioid receptor agonist is administered in a pharmaceutical composition comprising the delta opioid receptor agonist, or a pharmaceutically acceptable salt or ester thereof, and a pharmaceutically acceptable carrier.

3. The method according to claim 2 wherein the composition is administered by an administration modality selected from the group consisting of: oral, rectal, vaginal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

4. The method according to claim 3, wherein the composition is administered in a unitary dose form.

5. The method according to claim 1, wherein the pharmaceutical composition for combating the urinary tract dysfunction, further comprises at least one additional active agent that combats the urinary tract dysfunction selected from the group consisting of phenylpropanolamine, pseudoephedrein, oxybutynin, propantheline, dicyclomine, tolterodine, prazosin, terazosin and doxazosin.

6. A method for reducing the effects of urinary tract dysfunctions in a subject in need thereof comprising: administering to the subject an effective amount of at least one delta opioid receptor agonist selected from the group consisting of:

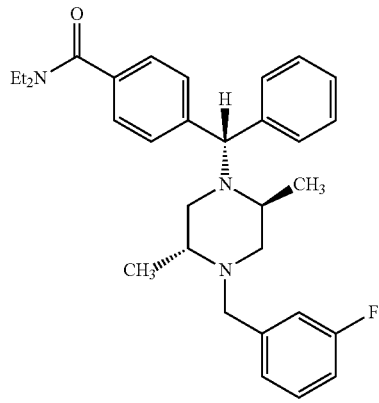

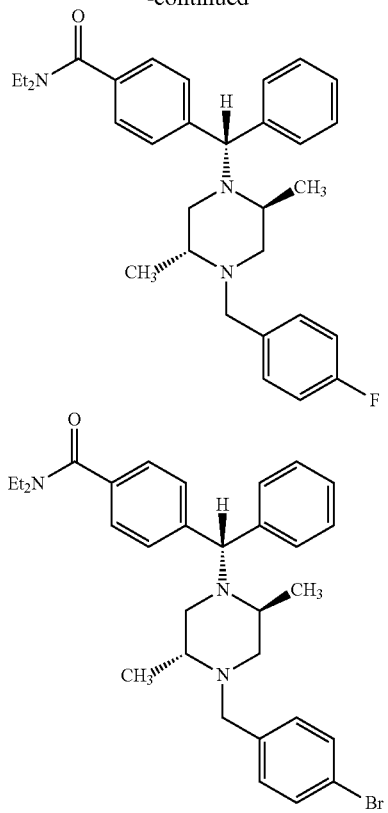

and pharmaceutically acceptable salts and esters thereof, wherein the urinary tract dysfunction is urinary incontinence.

7. The method according to claim 6, wherein the delta opioid receptor agonist is combined with a pharmaceutically acceptable carrier.

8. The method according to claim 6, wherein the delta opioid receptor agonist is combined with an active agent used to treat urinary tract dysfunctions and is selected from the group consisting of: phenylpropanolamine, pseudoephedrein, oxybutynin, propantheline, dicyclomine, tolterodine, prazosin, terazosin and doxazosin.

* * * * *